United States Patent
Yamada et al.

(10) Patent No.: US 11,299,524 B2
(45) Date of Patent: Apr. 12, 2022

(54) KIF13B-DERIVED PEPTIDE AND METHOD OF INHIBITING ANGIOGENESIS

(71) Applicant: THE BOARD OF TRUSTEES OF THE UNIVERSITY OF ILLINOIS, Urbana, IL (US)

(72) Inventors: Kaori Yamada, Lombard, IL (US); Asrar Malik, Hinsdale, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 57 days.

(21) Appl. No.: 16/325,006

(22) PCT Filed: Aug. 31, 2017

(86) PCT No.: PCT/US2017/049584
§ 371 (c)(1),
(2) Date: Feb. 12, 2019

(87) PCT Pub. No.: WO2018/045155
PCT Pub. Date: Mar. 8, 2018

(65) Prior Publication Data
US 2019/0169241 A1    Jun. 6, 2019

Related U.S. Application Data

(60) Provisional application No. 62/383,070, filed on Sep. 2, 2016, provisional application No. 62/510,536, filed on May 24, 2017.

(51) Int. Cl.
| | | |
|---|---|---|
| *A61K 38/00* | (2006.01) | |
| *A61P 9/00* | (2006.01) | |
| *C07K 14/435* | (2006.01) | |
| *C12N 9/14* | (2006.01) | |
| *C07H 23/00* | (2006.01) | |
| *A61K 47/54* | (2017.01) | |
| *A61K 38/17* | (2006.01) | |

(52) U.S. Cl.
CPC ............ *C07K 14/435* (2013.01); *A61K 38/00* (2013.01); *A61K 38/17* (2013.01); *A61K 47/543* (2017.08); *A61K 47/549* (2017.08); *A61P 9/00* (2018.01); *C07H 23/00* (2013.01); *C12N 9/14* (2013.01); *C07K 2319/10* (2013.01)

(58) Field of Classification Search
None
See application file for complete search history.

(56) References Cited

U.S. PATENT DOCUMENTS

| | | | | |
|---|---|---|---|---|
| 4,966,848 A * | 10/1990 | Smith | ................. | C12N 9/1029 435/193 |
| 5,223,421 A * | 6/1993 | Smith | ................. | C12N 9/1029 435/193 |
| 5,837,218 A * | 11/1998 | Peers | ................. | A61K 51/088 424/1.69 |
| 2002/0098236 A1 | 7/2002 | Fischer | | |
| 2006/0040262 A1* | 2/2006 | Morris | ................. | C07K 14/47 435/6.11 |
| 2007/0010434 A1 | 1/2007 | Chiu | | |

OTHER PUBLICATIONS

Yamada et al. (2017) "Antiangiogenic Therapeutic Potential of Peptides Derived from the Molecular Motor KIF13B that Transports VEGFR2 to Plasmalemma in Endothelial Cells." American Journal of Pathology 187(1):214-224.
Extended European Search Report dated Mar. 13, 2020 for EP 17847538.0, filed Aug. 31, 2017.
Hanada et al. (2000) "GAKIN, a Novel Kinesin-like Protein Associates with the Human Homologue of the *Drosophila* Discs Large Tumor Suppressor in T Lymphocytes." Journal of Biological Chemistry 275(37):28774-28784.
Horiguchi et al. (2006) "Transport of PIP3 by GAKIN, a kinesin-3 family protein, regulates neuronal cell polarity." Journal of Cell Biology 174(3):425-436.
Yamada et al. (2014) "KIF13B regulates angiogenesis through Golgi to plasma membrane trafficking of VEGFR2." Journal of Cell Science 127:4518-4530.
Yamada et al. (2007) "Effector domain of human Dlg tumor suppressor acts as a switch that relieves auto-inhibition of kinesin-3 motor GAKIN/KIF13B." Biochemistry 46:10039-10045.
International Search Report and Written Opinion in PCT/US2017/049584 dated Jan. 8, 2018.

\* cited by examiner

*Primary Examiner* — Thomas S Heard
(74) *Attorney, Agent, or Firm* — Licata & Tyrrell P.C.

(57) ABSTRACT

A construct composed of a Kinesin-derived Angiogenesis Inhibitor peptide and one or more carrier moieties and/or stabilizing moieties is provided as are methods for inhibiting angiogenesis and treating a disease or condition characterized by excessive vascularity.

13 Claims, 3 Drawing Sheets

Specification includes a Sequence Listing.

KIF13B-DERIVED PEPTIDE AND METHOD OF INHIBITING ANGIOGENESIS

INTRODUCTION

This application is a U.S. National Stage Application of PCT/US2017/049584 filed Aug. 31, 2017 and claims benefit of priority to U.S. Provisional Patent Application Ser. No. 62/383,070, filed Sep. 2, 2016 and 62/510,536, filed May 24, 2017, the contents of which are incorporated herein by reference in their entireties.

This invention was made with government support under Grant Numbers HL060678, R01 HL045638, P01 HL077806, R01 HL090152, R01 HL118068 and R01 HL125350 awarded by the National Institutes of Health. The government has certain rights in the invention.

BACKGROUND

Vascular endothelial growth factor (VEGF) plays a critical role in the metastasis and growth of cancer by increasing nutrient blood supply secondary to formation of new blood vessels. VEGF signals through activation of the endothelial cell (EC) surface-localized high-affinity tyrosine kinase receptor VEGFR2 (a.k.a., Flk-1). Poor vessel growth and maintenance cause ischemia in myocardial infarction, stroke, and neurodegenerative- and obesity-associated disorders whereas excessive vascular growth is essential for metastasis and growth of cancer, inflammatory disorders, and retinal vascular diseases associated with diabetes and macular degeneration. Thus, angiogenesis is a key therapeutic target for these diseases. Anti-VEGF antibodies and kinase inhibitors prevent VEGFR2 signaling and EC migration. VEGF-blockade also prolongs survival in monotherapy or combined therapy in cancer patients; however the responses are variable and some patients are either refractory or in time acquire resistance.

VEGF[165] binding to VEGFR2 induces VEGFR2 homodimerization, autophosphorylation, and internalization of VEGFR2. The internalized VEGFR2 is ubiquitinated and degraded in lysosomes. VEGF, in addition to ligating the receptor, signals the polarized trafficking of newly synthesized VEGFR2 from Golgi apparatus to the plasma membrane to continuously restore the cell surface receptor pool for the next round of VEGF binding and receptor activation cycle. This is evident by findings that inhibition of VEGFR2 trafficking prevents VEGF-mediated neo-vascularization in ears of mice and vessel formation in MATRIGEL plugs in vivo. The requirement for transport of VEGFR2 to the EC surface is especially important in the outward sprouting tip ECs, which form filopodia as the vessels grows outward while the stalk ECs just below the tip cells undergo increased proliferation in response to VEGF. Thus, VEGFR2 localization in tip cells is essential for directional migration of ECs in newly forming vessels. In this respect, it has been shown that KIF13B (kinesin family member 13B) unidirectionally transports VEGFR2 along microtubules in response to VEGF (Yamada, et al. (2014) *J. Cell Sci.* 127:4518-30). Further, inhibition of VEGFR2 trafficking by depletion of KIF13B abrogates EC migration and sprouting angiogenesis; however, EC survival and proliferation are unaffected (Yamada, et al. (2014) *J. Cell Sci.* 127:4518-30). The tail of KIF13B has multiple domains for cargo-binding. Besides VEGFR2, KIF13B transports polarity determination factors such as PIP3. These cargoes bind distinct regions of KIF13B often by bridge proteins such as Centaurin-α.

Loss of the inner endothelial blood-retinal barrier and the resultant macular edema and damage are the major causes of eye disorder and blindness in elderly population. At present, these conditions, also known as age-related macular degeneration (AMD), are incurable. In addition, the neovascular form of AMD is characterized by growth of the blood vessels from the choroid, which penetrate through Bruch's membrane into the subretinal area. Some effective therapies to stem the common underlying cause of neovascular AMD are limited with the objective of hindering the vision loss by destroying new vessels arising in the choroid. Although current treatments with intravitreal injection of corticosteroids and anti-VEGF agents are effective in delaying progression of eye disease, they do not completely eliminate the risk of blindness. Therefore, novel and more potent therapies or combinational therapy approaches for treating eye disorders and preventing vision loss are needed.

SUMMARY OF THE INVENTION

This invention provides a construct composed of a 16 to 65 amino acid peptide having the amino acid sequence Thr-$Xaa_1$-$Xaa_2$-$Xaa_3$-Glu-Arg-$Xaa_4$-$Xaa_5$-Leu-Ile-$Xaa_6$-Arg-$Xaa_7$-$Xaa_8$-Val-$Xaa_9$ (SEQ ID NO:1) operably linked to (a) one or more carrier moieties, (b) one or more stabilizing moieties, or (c) a combination of (a) and (b), wherein $Xaa_1$ is Pro, Ala or Glu; $Xaa_2$ is Val, Ala or Ser; $Xaa_3$ is Asp or Asn; $Xaa_4$ is Leu or Val; $Xaa_5$ is Phe or Tyr; $Xaa_6$ is Leu or Val; $Xaa_7$ is Val, Ala or Thr; $Xaa_8$ is Thr or Ala and $Xaa_9$ is Gln or Arg. In some embodiments, the one or more carrier moieties include a cell penetrating peptide (e.g., a peptide of SEQ ID NO:4-60), a lipid, Vitamin $B_{12}$, or a combination thereof. In other embodiments, the one or more stabilizing moieties include a peptide, post-translational modification (e.g., N-terminal acetylation and/or C-terminal amidation), non-natural amino acid residue (e.g., a D-amino acid residue), a macromolecule (e.g., polyethylene glycol, polysialic acid, hydroxyethyl starch, albumin or an immunoglobulin fragment) or a combination thereof. In some embodiments, the construct includes the amino acid sequence TPVDERLFLIVRVTVQ (SEQ ID NO:3). An exemplary construct is SRGTPVDERLFLIVRVTVQLSHP-$NH_2$ (SEQ ID NO:113). A pharmaceutical composition containing the peptide and methods for inhibiting angiogenesis and treating a disease or condition in a subject characterized by excessive vascularity (e.g., an inflammatory disease, cancer, or retinal vasculopathy) are also provided.

and injected s.c. in C57BL6 mice. Data are expressed as means±SEM. N=4, 4, 5, and 5 for vector control, DUF2, DUF2C5, and $C_T$, respectively. *P<0.05 (one-way analysis of variance). $C_T$, residues 1528-1826 of KIF13B.

Figure 3:
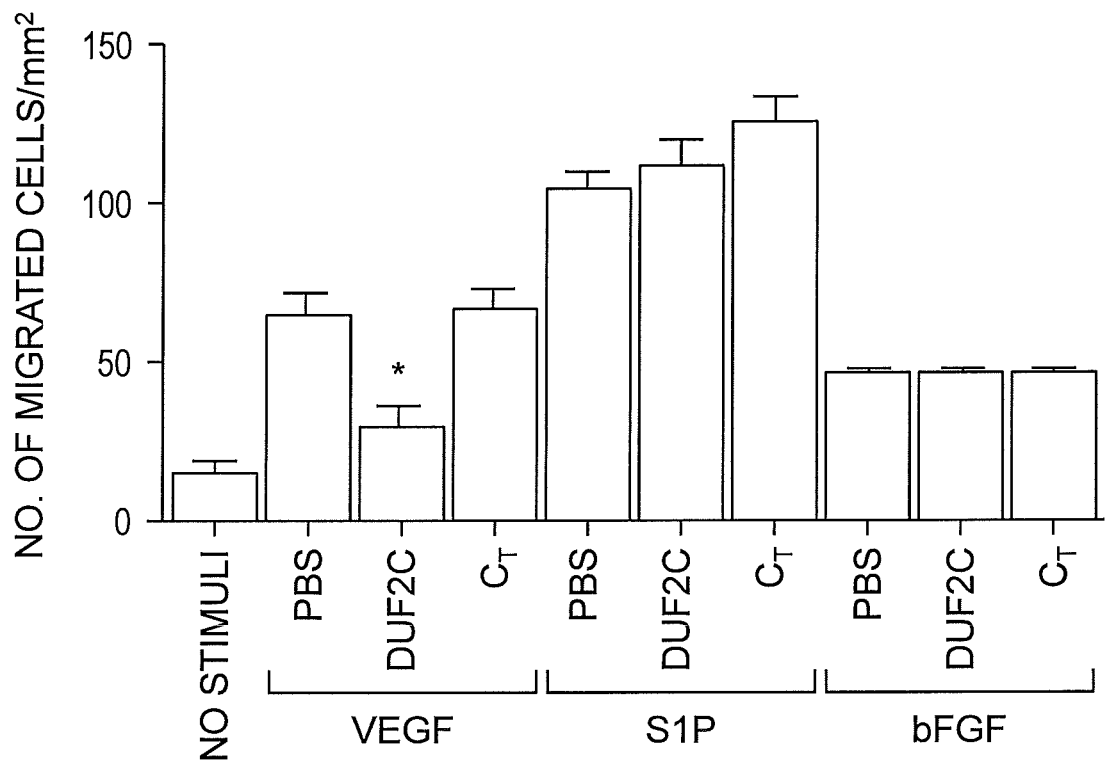

FIG. 3 shows that DUF2C5 inhibits vascular endothelial growth factor (VEGF)-induced endothelial cell (EC) migration. Specificity of the inhibitory effect of DUF2C5 was determined by EC migration induced by different stimuli in a TRANSWELL migration assay. HUVECs migrated toward 2.2 nmol/L VEGF, 50 ng/mL basic fibroblast growth factor (bFGF), or 1 µmol/L sphingosine-1-phosphate (S1P) were visualized by hematoxylin staining, and number of migrated cells were counted. Data are expressed as means±SEM. N=3. *P<0.05 (one-way analysis of variance and Bonferroni multiple comparisons test).

Figure 4A:
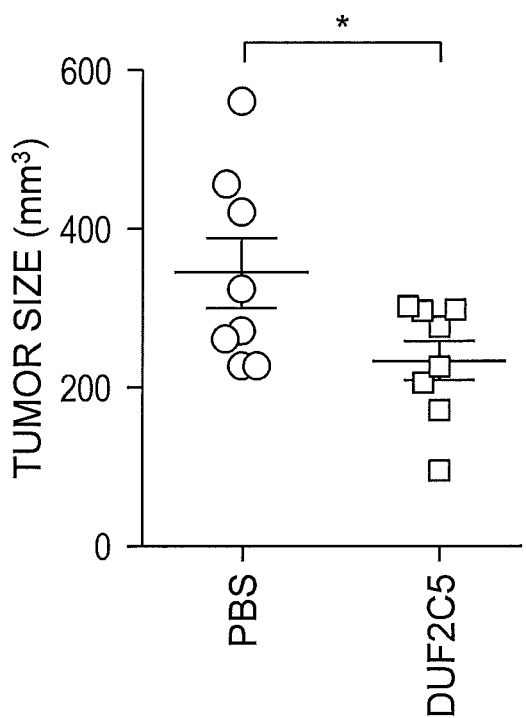
Figure 4B:
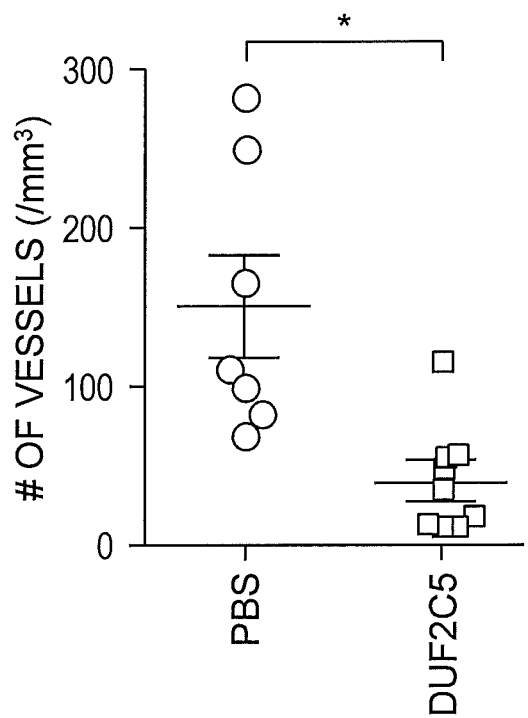

FIG. 4A and FIG. 4B show that DUF2C5 inhibits angiogenesis and tumor growth in vivo. FIG. 4A, Study of human lung carcinoma H460 xenograft in mice with severe combined immunodeficiency. Mice were treated with 10 mg/kg DUF2C5 (with C-terminal amidation) or phosphate-buffered saline (PBS), i.v. via tail vein, three times per week, and tumor size is shown in the graph. FIG. 4B, Number of vessels in tumor in PBS-treated control and peptide-treated tumor. Data are expressed as means±SEM. N=8 in each group. *P<0.05, **P<0.01 (t-test).

Figure 5A:
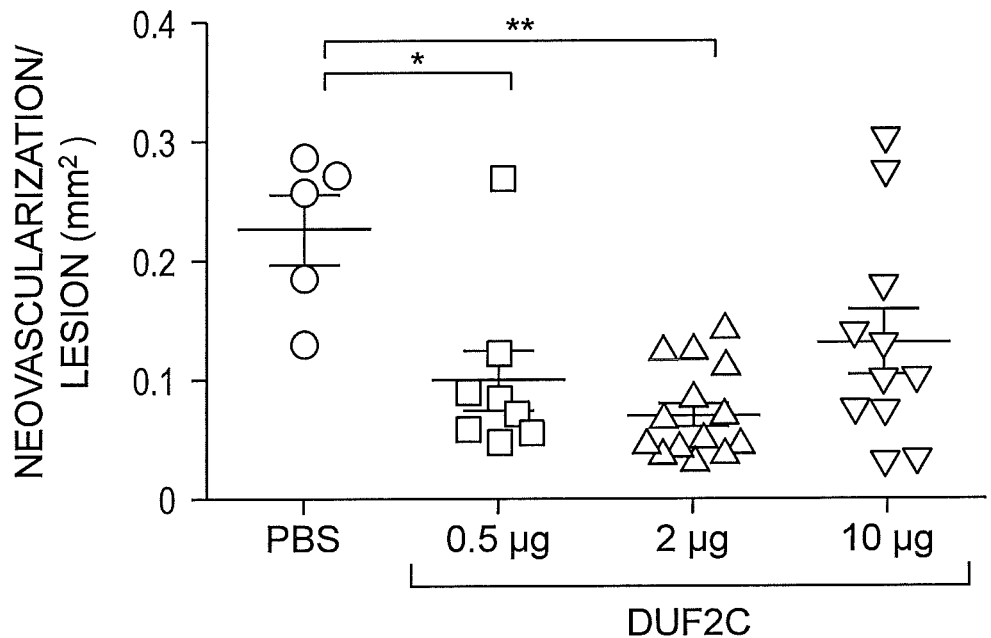
Figure 5B:
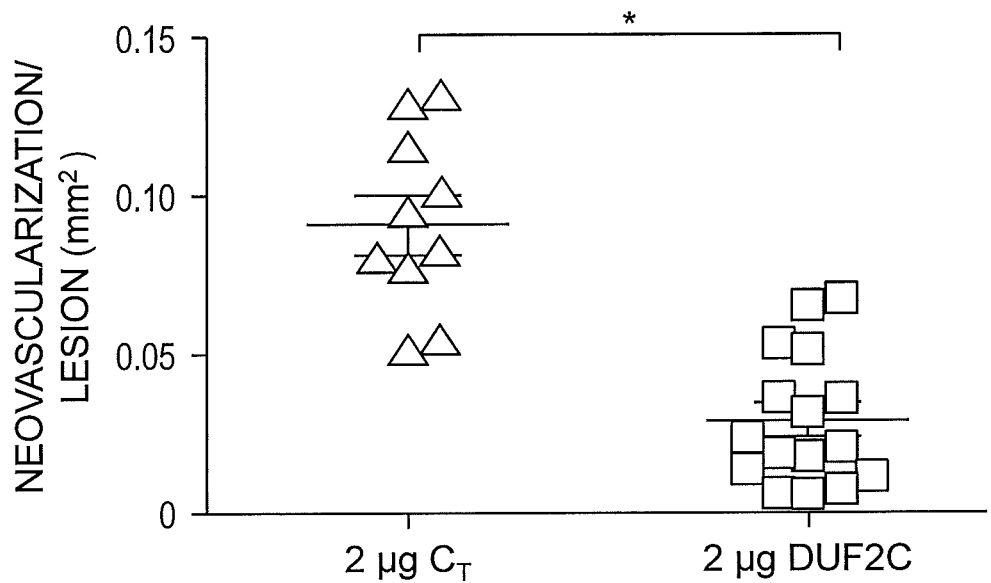

FIG. 5A and FIG. 5B show the effect of DUF2C5 treatment on laser-induced CNV. FIG. 5A, Dose-dependent effect of DUF2C5 was tested by intravitreal injection of DUF2C5 0.5 µg, 2 µg, and 10 µg after laser photocoagulation. Neovascularization was assessed by the area of ILB4-staining, and plotted in the graph (N=5 mice in each group, and 4 laser burns were induced in each mouse). Asterisks indicate p<0.05, One-way ANOVA. FIG. 5B, Effect of DUF2C5 as an eye drop was tested in CNV model. After laser photocoagulation, mice were treated daily with either control peptide (2 µg/eye) or DUF2C5 (2 µg/eye) for weeks. Neovascularization was assessed by the area of ILB4-staining, and plotted in the graph (N=7 mice in each group, and 4 laser burns were induced in each mouse). Asterisks indicate p<0.05, t-test.

DETAILED DESCRIPTION OF THE INVENTION

The delivery of VEGFR2 to the endothelial plasma membrane is a key determinant of angiogenesis. The effectiveness of VEGFR2 signaling depends on its localization at the surface of endothelial cells. This is evident in sprouting tip cells in which there is continuous cycling of VEGFR2 from the Golgi to the cell surface pool of VEGFR2. VEGFR2 transport to the cell surface is thus needed for each round of ligation by VEGF. The molecular motor kinesin KIF13B has been shown to transport VEGFR2 to the cell surface (Yamada, et al. (2014) *J. Cell Sci.* 127:4518-30). A Kinesin-derived Angiogenesis Inhibitor (KAI) peptide (designated in the Examples as DUF2C5) has now been found, which dominant-negatively inhibits defective angiogenesis. The KAI peptide prevents VEGFR2 trafficking to the cell surface, a characteristic that is specific for VEGF-induced endothelial cell sprouting because KAI did not affect endothelial cell migration induced by SIP or bFGF. In addition, the KAI peptide inhibits VEGF-induced capillary network formation in vitro and neo-vascularization in vivo. Advantageously, the KAI peptide is cationic, based on its amino acid composition, is water soluble (>10 mg/mL), and cell permeable because of its cationic nature. Further, the KAI peptide is not itself toxic to endothelial cells, and mice treated i.v. with the peptide do not experience any untoward effects.

Accordingly, the present invention provides a peptide construct containing the KAI peptide, and methods of using this construct for the treatment of angiogenesis-related diseases, such as cancer and diabetic retinopathy. For the purposes of this invention, the term "construct" is used herein to refer to a KAI peptide that has been modified by recombinant, chemical and/or enzymatic techniques to include one or more moieties that enhance uptake, stability and/or solubility of the peptide. In particular, at least one of the one or more moieties is not naturally associated with the KAI peptide. Ideally, a construct of the invention is a KAI peptide having the amino acid sequence of SEQ ID NO:1 operably linked to one, two, three, four or more carrier moieties. Alternatively, a construct of the invention is a KAI peptide having the amino acid sequence of SEQ ID NO:1 operably linked to one, two, three, four or more stabilizing moieties. Moreover, a construct of the invention is a KAI peptide having the amino acid sequence of SEQ ID NO:1 operably linked to one or more carrier moieties and one or more stabilizing moieties. In some embodiments, a single modification (e.g., N-acetylation) can function as both a carrier moiety and stabilizing moiety.

The term "peptide," as used herein, refers broadly to a sequence of two or more amino acids joined together by peptide bonds. It should be understood that this term does not connote a specific length of a polymer of amino acids, nor is it intended to imply or distinguish whether the peptide is produced using recombinant techniques, chemical or enzymatic synthesis or is naturally occurring. The KAI peptide of the construct of this invention is composed of at least 16, 17, 18, 19, 20, 21, 22, 23, 24, 25 to 65 amino acid residues, including all ranges derivable therein. Provided that binding to the VEGFR2 receptor is retained, shorter peptides in the range of 6 to 16 amino acid residues are also contemplated. Ideally, the KAI peptide provides a minimum binding site for VEGFR2 trafficking and does not exhibit a significant affinity for other receptor tyrosine kinases (e.g., PDGFRα, PDGFRβ, and EGFR). In particular, the KAI peptide comprises or consists of the amino acid sequence Thr-Xaa$_1$-Xaa$_2$-Xaa$_3$-Glu-Arg-Xaa$_4$-Xaa$_5$-Leu-Ile-Xaa$_6$-Arg-Xaa$_7$-Xaa$_8$-Val-Xaa$_9$ (SEQ ID NO:1), wherein Xaa$_1$ is Pro, Ala or Glu; Xaa$_2$ is Val, Ala or Ser; Xaa$_3$ is Asp or Asn; Xaa$_4$ is Leu or Val; Xaa$_5$ is Phe or Tyr; Xaa$_6$ is Leu or Val; Xaa$_7$ is Val, Ala or Thr; Xaa$_8$ is Thr or Ala and Xaa$_9$ is Gln or Arg. More preferably, the KAI peptide comprises or consists of the amino acid sequence Thr-Pro-Xaa$_1$-Asp-Glu-Arg-Xaa$_2$-Xaa$_3$-Leu-Ile-Xaa$_4$-Arg-Val-Xaa$_5$-Val-Xaa$_6$ (SEQ ID NO:2), wherein Xaa$_1$ is Val, Ala or Ser; Xaa$_2$ is Leu or Val; Xaa$_3$ is Phe or Tyr; Xaa$_4$ is Leu or Val; Xaa$_5$ is Thr or Ala; and Xaa$_6$ is Gln or Arg. Exemplary KAI peptides of the invention are set forth herein in SEQ ID NO:3 and SEQ ID NOs:80-93 (see Table 4). Most preferably, the KAI peptide comprises or consists of the amino acid sequence Thr-Pro-Val-Asp-Glu-Arg-Leu-Phe-Leu-Ile-Val-Arg-Val-Thr-Val-Gln (also referred to herein using the conventional one-letter abbreviations as TPVDERLFLIVRVTVQ) (SEQ ID NO:3).

As used herein, "carrier moiety" refers to a polypeptide, polynucleotide, carbohydrate, or organic or inorganic molecule that facilitates traversing a lipid bilayer, micelle, cell membrane, organelle membrane, or vesicle membrane. A carrier moiety attached to another molecule facilitates the molecule traversing a membrane, for example going from extracellular space to intracellular space, or cytosol to within an organelle. In some cases, a carrier moiety facilitates crossing the blood-brain barrier. In some embodiments, a carrier moiety is covalently linked to the amino terminus of the KAI peptide. In other embodiments, a carrier moiety is covalently linked to the carboxyl terminus of the KAI peptide. Ideally, the carrier moiety is a cell penetrating peptide, a lipid, vitamin $B_{12}$, or a combination thereof.

Cell-penetrating peptides (CPP), also known as peptide transduction domains (PTD), are a diverse class of peptides that have been reported to traverse the cell membrane. Representative members of this family such as the Trans-Activator of Transcription (TAT) peptide and penetratin were initially identified as segments within naturally occurring proteins with proposed membrane permeability. In some cases, the carrier moiety is a cell-penetrating peptide that is covalently linked or fused to the KAI peptide. In some embodiments, the covalent linkage is a peptide bond. For example, the cell-penetrating peptide can be a peptide having a length of from about 5 to about 50 amino acids, e.g., from about 5 to about 10 amino acids, from about 10 to about 15 amino acids, from about 15 to about 20 amino acids, from about 20 to about 25 amino acids, from about 25 to about 30 amino acids, from about 30 to about 40 amino acids, or from about 40 to about 50 amino acids.

Cell-penetrating peptides are well-known in the art and are described by, e.g., Bechara & Sagan (2013) *FEBS Lett.* 587:1693-1702; Copolovici, et al. (2014) *ACS Nano* 8(3): 1972-94; and Guidotti, et al. (2017) *Trends Pharmacol. Sci.* 38(4):406-24. Exemplary cell-penetrating peptides of use in this invention include, but are not limited to, the peptides listed in Table 1.

TABLE 1

| CPP | Sequence | SEQ ID NO: |
|---|---|---|
| Antennapedia | RQIKIWFQNRRMKWKK | 4 |
| DAT | FREKLAYIAP | 5 |
| DPV3 | RKKRRRESRKKRRRES | 6 |
| DPV6 | GRPRESGKKRKRKRLKP | 7 |
| DPV7 | GKRKKKGKLGKKRDP | 8 |
| DPY7b | GKRKKKGKLGKKRPRSR | 9 |
| DPV3/10 | RKKRRRESRRARRSPRHL | 10 |
| DPV10/6 | SRRARRSPRESGKKRKRKR | 11 |
| DPV1047 | VKRGLKLRHVRPRVTRMDV | 12 |
| DPV1048 | VKRGLKLRHVRPRVTRDV | 13 |
| DPV10 | SRRARRSPRHLGSG | 14 |
| DPV15 | LRRERQSRLRRERQSR | 15 |
| DPV15b | GAYDLRRRERQSRLRRRERQSR | 16 |
| DPV51 | KRGLKLRH | 17 |
| Buforin II | TRSSRAGLQFPVGRVHRLLRK | 18 |
| GALA | WEAALAEALAEALAEHLAEALAEALEALAA | 19 |
| Cβ | KGSWYSMRKMSMKIRPFFPQQ | 20 |
| preCγ | KTRYYSMKKTTMKIIPFNRL | 21 |
| CαE | RGADYSLRAVRMKIRPLVTQ | 22 |
| hCT(9-32) | LGTYTQDFNKFHTFPQTAIGVGAP | 23 |
| HN-1 | TSPLNIHNGQKL | 24 |
| Influenza virus nucleoprotein (NLS) | NSAAFEDLRVLS | 25 |
| KALA | WEAKLAKALAKALAKHLAKALAKALKACEA | 26 |
| K-FGF | AAVALLPAVLLALLAP | 27 |
| Ku70 | VPMLKPMLKE | 28 |
| MAP | KLALKLALKALKAALKLA | 29 |
| MPG | GALFLGFLGAAGSTMGAWSQPKKKRKV | 30 |

TABLE 1-continued

| CPP | Sequence | SEQ ID NO: |
|---|---|---|
| MPM (IP/K-FGF) | AAVALLPAVLLALLAP | 31 |
| N50 (NLS of NF-κB P50) | VQRKRQKLM | 32 |
| Pep-1 | KETWWETWWTEWSQPKKKRKV | 33 |
| Pep-7 | SDLWEMMMVSLACQY | 34 |
| Penetratin | RQIKIWFQNRRMKWKK | 35 |
| Short Penetratin | RRMKWKK | 36 |
| Polyarginine - $R_7$ | RRRRRRR | 37 |
| Polyarginine - $R_9$ | RRRRRRRRR | 38 |
| pISL | RVIRVWFQNKRCKDKK | 39 |
| Prion mouse $PrPc_{1-28}$ | MANLGYWLLALFVTMWTDVGLCKKRPKP | 40 |
| pVEC | LLIILRRRIRKQAHAHSK | 41 |
| $R_6W_3$ | RRWWRRWRR | 42 |
| SAP | VRLPPPVRLPPPVRLPPP | 43 |
| SV-40 (NLS) | PKKKRKV | 44 |
| SynB1 | RGGRLSYSRRRFSTSTGR | 45 |
| SynB3 | RRLSYSRRRF | 46 |
| SynB4 | AWSFRVSYRGISYRRSR | 47 |
| $Tat_{47-60}$ | YGRKKRRQRRRPPQ | 48 |
| $Tat_{47-57}$ | YGRKKRRQRRR | 49 |
| $Tat_{49-57}$ | RKKRRQRRR | 50 |
| $Tat_{49-60}$ | GRKKRRQRRRPPQ | 51 |
| Transportan | GWTLNSAGYLLGKINLKALAALAKKTL | 52 |
| Transportan 10 | AGYLLGKINLKALAALAKKIL | 53 |
| Transportan derivative | GWTLNSAGYLLG | 54 |
| Short Transportan | INLKALAALAKKTL | 55 |
| VP22 | DAATATRGRSAASRPTERPRAPARSASRPRRPVD | 56 |
| VT5 | DPKGDPKGVTVTVTVTGKGDPKPD | 57 |

As described in Example 6, the DUF2C5 peptide itself can traverse the cell membrane. Enhanced cell penetration of the DUF2C5 peptide was attributed to the three N-terminal amino acid residues, Ser-Arg-Gly (SEQ ID NO:58). Accordingly, in some cases, the cell penetrating peptide is derived from the native KIF13B protein sequence. A cell penetrating peptide derived from the KIF13B sequence preferably has the amino acid sequence $Xaa_1$-$Xaa_2$-$Xaa_3$ (SEQ ID NO:59), wherein $Xaa_1$ is Ser or Asn; $Xaa_2$ is Lys or Arg and $Xaa_3$ is Gly or Val. More preferably, the cell penetrating peptide has the amino acid sequence Ser-$Xaa_1$-Gly (SEQ ID NO:60), wherein $Xaa_1$ is Lys or Arg. Most preferably, the cell penetrating peptide has the amino acid sequence Ser-Arg-Gly (SEQ ID NO:58).

Alternatively or in addition to, the KAI peptide can include a lipid to facilitate cell penetration. As used herein, lipids generally refer to water insoluble molecules soluble in organic solvents. In some embodiments, a lipid is a fatty acid, which includes an aliphatic hydrocarbon chain with an acyl group, where the aliphatic chain is either a saturated or an unsaturated alkyl with one or more double bonds. Typical fatty acids include, without limitation, lauric acid, myristic acid, palmitic acid, stearic acid, oleic acid, linoleic acid, and linolenic acid. Fatty acids are or could be linked to acyl group carriers, such as glycerol, sphingosine, cholesterol, and others.

Lipids can also be classified into different lipid classes based on their polarity. Lipids may be nonpolar or polarlipids. Examples of such non-polar lipids are mono-, di- or triacylglycerols (glycerides), alkyl esters of fatty acids, and fatty alcohols. Polar lipids have polar head groups and exhibit surface activity, such as fatty amines, phosphatidic acid (e.g., phosphatidyl ethanolamine, phosphatidyl choline, etc.), phospholipids, glycolipids glycosylphosphatidylinositol), and the like. In certain forms, the lipids are attached to or linked to nucleosides, nucleotides, nucleic acids, amino acid, proteins, or saccharides. Exemplary lipids that can be attached to the KAI peptide include N-myristoyl, palmitoyl, and glycophosphatidyl inositol (see, e.g., Thompson & Okuyama (2000) *Prog. Lipid Res.* 39:19-39; Bauman & Menon (2002) In: *Biochemistry of lipids*, lipoproteins and membranes, 4th Edition, pp. 37-54, Nance & Vance Ed., Elsevier, Amsterdam). Preferably, the KAI peptide is myristylated, stearylated or palmitoylated at the N-terminal amino acid residue. More preferably, the KAI peptide is myristylated at the N terminal amino acid residue.

As used herein, a lipid can also be a steroid, a tetracyclic compound based on hydrogenated 1,2 cyclopentenophenanthrene having substituents at the C-10, C-13 and C-17 carbon atoms. Typical steroids include, but are not limited to, cholic acid, desoxycholic acid, chenodesoxycholic acid, estrone, progesterone, testosterone, androsterone, norethindrone, cholesterol, digoxin, and the like. Steroid or sterols as described herein may be attached to or modified with nucleosides, nucleotides, nucleic acids, amino acids, proteins, saccharides, oligosaccharides, polysaccharides, and other lipids.

Moreover, a lipid can also include an isoprenoid composed of isoprene units $C_5H_8$. Isoprenoids include various naturally occurring and synthetic terpenes, which may be either linear, or more typically cyclic, including bicylic, tricyclic and polycyclic. Exemplary isoprenoids include, by way of example, geraniol, citronellal, zingiberene, β-santanol, β-cadiene, matricarin, copaene, camphene, taxol, carotenoids, steroids, and the like. Isoprenoids may be attached to other molecules, including, but not limited to, nucleosides, nucleotides, nucleic acids, amino acids, proteins, saccharides, oligosaccharides, and polysaccharides. By way of illustration, a prenylated peptide can be prepared by attachment of isoprenoid lipid units, farnesyl ($C_{15}$) or geranylgeranyl ($C_{20}$), via cysteine thio-ether bonds at or near the carboxyl terminus of the KAI peptide. The use of Reversible Aqueous Lipidization Technology (REAL) is also contemplated. See Mahajan, et al. (2014) *Indian J. Pharmaceut. Ed. Res.* 48:34-47.

Specific uptake mechanisms exist in the gastrointestinal tract for uptake of dietary molecules. In the case of Vitamin $B_{12}$, a specific binding protein is released into the intestine which binds to its ligand in the lumen of the gut. Mammals have a transport mechanism for the absorption and cellular uptake of the relatively large Vitamin $B_{12}$ molecule which relies upon complexing to a naturally occurring transport protein known as Intrinsic Factor. Taking advantage of this transport mechanism, Vitamin $B_{12}$ has been coupled to the D-Lys-6-analog of luteinizing hormone releasing hormone via a carboxyl group of an acid-hydrolyzed propionamide side chain and shown to deliver the luteinizing hormone releasing hormone analog into the blood (see U.S. Pat. Nos. 5,428,023 and 5,807,832). Likewise, U.S. Pat. No. 5,574,018 teaches Vitamin $B_{12}$ conjugated to erythropoietin, granulocyte colony stimulating factor and consensus interferon through covalent binding at the primary hydroxyl site of the ribose moiety of the Vitamin $B_{12}$. Further, US 2011/0092416 teaches coupling of Vitamin $B_{12}$ to a therapeutically active polypeptide such as insulin, peptide tyrosine-tyrosine (PYY), neuropeptide Y (NPY) and Glucagon-like peptide-1 (GLP-1), wherein the polypeptide is covalently attached to a dicarboxylic acid derivative of the primary (5') hydroxyl group of the ribose moiety of Vitamin $B_{12}$. Moreover, WO 2016/187512 teaches that conjugation of Vitamin $B_{12}$ to azidolysine at position 12 of GLP-1 and subsequent complexation with Intrinsic Factor protects this peptide from protease degradation. Accordingly, in certain embodiments, the KAI peptide is conjugated to Vitamin $B_{12}$.

Alternatively, the KAI peptide can include other modifications to facilitate cellular uptake. For example, cyclizing a given peptide and/or methylating select amide bond nitrogens may improve its membrane permeation and/or bioavailability. Such modifications, when made judiciously, are thought to facilitate the formation of intramolecular hydrogen bonds in response to the low dielectric environment of the membrane interior (Bockus, et al. (2013) *Curr. Top. Med. Chem.* 13:821-836; Rezai, et al. (2006) *J. Am. Chem. Soc.* 128:14073-14080; White, et al. (2011) *Nat. Chem. Biol.* 7:810-817). In addition to permeability, cyclization can increase stability. Indeed, a cyclic version of DUF2C5 was found to be stable and bind to VEGFR2, whereas a control cyclic peptide did not bind. Accordingly, in certain embodiments, the KAI peptide of this invention is cyclized. The KAI peptide can be cyclized head-to-tail, head/tail-to-side-chain, or side-chain-to-side-chain. Cyclization is commonly accomplished through lactamization, lactonization, and sulfide-based bridges.

A variety of inorganic materials have also been proposed to translocate protein cargo, including silica, carbon nanotubes, quantum dots, and gold nanoparticles (Du, et al. (2012) *Curr. Drug Metab.* 13:82-92; Malmsten (2013) *Curr. Opin. Colloid Interface Sci.* 18:468-480). In addition, N-methylation can be used to reduce hydrogen bonding potential.

As used herein, "stabilizing moiety" refers to a polypeptide, polynucleotide, carbohydrate, or organic or inorganic molecule that reduces proteolysis, reduces renal clearance, increases oral bioavailability, increases binding to VEGFR2, and/or prolongs half-life of the KAI peptide. In some embodiments, a stabilizing moiety is covalently linked to the amino terminus of the KAI peptide. In other embodiments, a stabilizing moiety is covalently linked to the carboxyl terminus of the KAI peptide. Ideally, the stabilizing moiety is a peptide, post-translational modification, non-natural amino acid residue, a macromolecule or a combination thereof.

In some embodiments, the stabilizing moiety can be a peptide derived from the native KIF13B protein sequence. A stabilizing moiety derived from the KIF13B sequence preferably has, e.g., the amino acid sequence Leu-Ser-His-Pro (SEQ ID NO:61) or Leu-Ser-His-Pro-Ala-Asp (SEQ ID NO:62).

A number of proteolytic enzymes in blood/plasma, liver or kidney break down peptide sequences from the N- and/or C-termini. Post-translational modification of the N- or/and C-termini can often improve peptide stability. For example, N-acetylation and C-amidation can increase resistance to proteolysis. For example, N-terminal acetylated somatostatin analogs were reported to be much more stable than the native peptide (Adessi & Soto (2002) *Curr. Med. Chem.* 9(9):963-78). Similarly, the N-acetylated 7-34 form of GLP-1 has been shown to be much more stable than the unprotected peptides (John, et al. (2008) *Eur. J. Med. Res.* 13(2):73-8). In addition, N-acetylation and C-amidation improve resistance against endopeptidase digestion of EFK17 peptide when applied in conjunction with amino acid substitutions (Stroemstedt, et al. (2009) *Antimicrob. Agents Chemother.* 53(2):593-602). Moreover, Tesamorelin, having a hexenoyl group attached to the N-terminal tyrosine residue, has a much longer half-life than the natural growth hormone-releasing hormone (Ferdinandi, et al. (2007) *Basic Clin. Pharmacol. Toxicol.* 100(1):49-58). In certain embodiments, the KAI peptide includes N-acetylation and/or C-amidation as stabilizing moieties.

Substituting natural amino acid residues with non-natural residues can decrease the substrate recognition and binding affinity of proteolytic enzymes and increase stability. For example, replacing L-Arg of vasopressin with D-Arg example increased the half-life of this peptide from 10-35 minutes in humans to 3.7 hours in healthy human volunteers (Agerso et al. (2004) *Br. J. Clin. Pharmacol.* 58(4):352-8). Similarly, the substitution of L-amino acids with D-amino acids improves the in vivo half-life of somatostatin from a few minutes to 1.5 hours (Harris (1994) *Gut* 35(3):S1-4). Modification of natural amino acids can also improve the stability of peptides by introducing steric hindrance. For example, gonadotropin-releasing hormone has a very short half-life (minutes), while buserelin, in which one Gly is replaced with a t-butyl-d-Ser and another Gly is substituted by ethylamide, has a much longer half-life in humans. Ipamorelin, a pentapeptide, has 2'-naphthylalanine and phenylalanine in the D configuration and the C-terminal L-alanine replaced by 2-aminoisobutyric acid, resulting in improved terminal half-life of about 2 hours in humans (Raun, et al. (1998) *Eur. J. Endocrinol.* 139(5):552-61; Gobburu, et al. (1999) *Pharm. Res.* 16(9):1412-6).

Conjugation to macromolecules (e.g., polyethylene glycol (PEG) or albumin) is an effective strategy to improve stability of peptides and reduce renal clearance. For example, covalently attaching albumin-binding small molecules to peptides can reduce glomerular filtration, improve proteolytic stability, and prolong half-life by indirectly interacting with albumin through the highly bound small molecules. Liraglutide is a GLP-1 analog that is linked via a γ-1-glutamyl spacer to a 16-carbon fatty acid residue. The lipopeptide binds to albumin, thus decreasing proteolysis and renal clearance and increasing half-life from a few minutes to 8 hours (Hou, et al. (2012) *J. Cereb. Blood Flow Metab.* 32(12):2201-10; Levy Odile, et al. (2014) *PLoS One* 9(2):e87704; Lindgren, et al. (2014) *Biopolymers* 102(3): 252-9).

Conjugation of peptides to large synthetic or natural polymers or carbohydrates can increase their molecular weight and hydrodynamic volume, thus reducing their renal clearance. The common polymers used for peptide conjugation are PEG, polysialic acid (PSA), and hydroxyethyl starch (HES). An example is peginesatide, a PEGylated synthetic peptide, which has an elimination half-life of 18.9 hours in healthy volunteers (Bronson, et al. (2013) *Annu. Rep. Med. Chem.* 48:471-546). As used herein, "Polyethylene glycol" or "PEG" is a poly ether compound of general formula H—(O—CH$_2$—CH$_2$)$_n$—OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 Da, PEO to polymers with a molecular mass above 20,000 Da, and POE to a polymer of any molecular mass. The polymeric moiety is preferably water-soluble (amphiphilic or hydrophilic), nontoxic, and pharmaceutically inert. Suitable polymeric molecules of use as stabilizing moieties include polyethylene glycols (PEG), homo- or co-polymers of PEG, a monomethyl-substituted polymer of PEG (mPEG), or poly oxy ethylene glycerol (POG). Also encompassed are PEGs that are prepared for purpose of half life extension, for example, mono-activated, alkoxy-terminated polyalkylene oxides (POA's) such as mono-methoxy-terminated polyethyelene glycols (mPEG's); bis-activated polyethylene oxides (glycols) or other PEG derivatives are also contemplated. Suitable polymers will vary substantially by weights ranging from about 200 Da to about 40,000 Da or from about 200 Da to about 60,000 Da are usually selected for the purposes of the present invention. In certain embodiments, PEGs having molecular weights from 200 to 2,000 or from 200 to 500 are used.

PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear. The numbers that are often included in the names of PEGs indicate their average molecular weights (e.g., a PEG with n=9 would have an average molecular weight of approximately 400 daltons, and would be labeled PEG 400). As used herein, "PEGylation" is the act of covalently coupling a PEG structure to the KAI peptide of the invention, which is then referred to as a "PEGylated KAI peptide." In certain embodiments, the PEG of the PEGylated side chain is a PEG with a molecular weight from about 200 to about 40,000.

Plasma proteins, such as albumin and immunoglobulin (IgG) fragments, have long half-lives of 19-21 days in humans (Pollaro & Heinis (2010) *Med. Chem. Comm.* 1(5):319-24). Because of the high MW (67-150 kDa), these proteins have low renal clearance, and their binding to neonatal Fc receptor (FcRn) reduces the elimination through pinocytosis by the vascular epithelium. Covalent linkage of a KAI peptide to albumin or IgG fragments can reduce renal clearance and prolong half-life. By way of illustration, the albumin-exendin-4 conjugate (CJC-1134-PC) has a half-life of ~8 days in humans and the FDA-approved drug, albiglutide, is a DPPIV-resistant GLP-1 dimer fused to human albumin, which has a half-life of 6-7 days thereby enabling weekly dosing for the treatment of type 2 diabetics (Pratley, et al. (2014) *Lancet Diabetes Endocrinol.* 2(4):289-97).

When the carrier moiety and/or stabilizing moiety is a peptide, said peptide can be readily attached or conjugated directly to the KAI peptide via a peptide bond. However, in cases where the carrier moiety and/or stabilizing moiety is not a peptide, said carrier moiety and/or stabilizing moiety can be attached to the KAI peptide by other conventional linkages such as disulfide, amide, oxime, thiazolidine, urea and carbonyl linkages, or Diels-Alder or Hüisgen 1,3-dipolar cycloaddition reactions (Lu, et al. (2010) *Bioconjug. Chem.* 21:187-202; Roberts, et al. (2002) *Adv. Drug Deliv. Rev.* 54:459-76; WO 2008/101017).

Alternatively, the construct of this invention can include a linker to join or link a carrier moiety and/or stabilizing moiety to the KAI peptide. For the purposes of this invention, a linker is a peptide having any of a variety of amino acid sequences. A linker which is a spacer peptide, can be of a flexible nature, although other chemical linkages are not excluded. A linker peptide can have a length of from about 1 to about 40 amino acids, e.g., from about 1 to about 5 amino acids, from about 5 to about 10 amino acids, from about 10 to about 20 amino acids, from about 20 to about 30 amino acids, or from about 30 to about amino acids, in length. These linkers can be produced using synthetic, linker-encoding oligonucleotides to couple the proteins. Peptide linkers with a degree of flexibility can be used. The linking peptides may have virtually any amino acid sequence, where in some embodiments the linker peptide will have a sequence that results in a generally flexible peptide. The use of small amino acids, such as glycine and alanine, are of use in creating a flexible peptide. The creation of such sequences is routine to those of skill in the art. Various linkers are commercially available and are considered suitable for use.

Exemplary flexible linkers, which can be used to join or link a carrier moiety and/or stabilizing moiety to the KAI peptide, include glycine polymers $(G)_n$, (e.g., where n is an integer from 1 to about 20); glycine-serine polymers (including, for example, $(GS)_n$, $GSGGS_n$ (SEQ ID NO:63) and $GGGS_n$ (SEQ ID NO:64), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are used in some embodiments. See Scheraga (1992) *Rev. Computational Chem.* 11173-142. Exemplary flexible linkers include, but are not limited to GG, GGG, GGS, GGSG (SEQ ID NO:65), GGSGG (SEQ ID NO:66), GSGSG (SEQ ID NO:67), GSGGG (SEQ ID NO:68), GGGSG (SEQ ID NO:69), GSSSG (SEQ ID NO:70), and the like.

Non-peptide linker moieties can also be used to join or link a carrier moiety and/or stabilizing moiety to the KAI peptide. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to peptides may be used in light of this disclosure.

Exemplary constructs including the KAI peptide operably linked, conjugated or joined to one or more carrier moieties and/or one or more stabilizing moieties are provided herein. See, e.g., Examples 7-8 and SEQ ID NOs:94-138. However, without departing from the scope of this invention, the construct also encompasses KAI peptides having one or more deletions, additions, and/or substitutions in the KAI peptide of SEQ ID NO:1, which retain at least one functional property of the peptide. For example, the KAI peptide of SEQ ID NO:1 may be modified in that the amino acid sequence has one or more conserved amino acid substitutions, amino acid insertions, amino acid deletions, carboxyterminal truncation, or an amino-terminal truncation. In certain embodiments, one skilled in the art may identify suitable areas of the KAI peptide that may be changed without destroying activity by targeting regions not believed to be important for activity. In further embodiments, even amino acid residues important for biological activity or for structure may be subject to conservative amino acid substitutions without destroying the biological activity thereof or without adversely affecting the peptide structure. For example, Arg may be replaced by Lys and/or Thr may be replaced by Ser at one or more occurrences. In one embodiment, a variant KAI peptide has at least 50%, 60%, 70%, 80%, 90%, 95%, 98%, 99% amino acid sequence identity with the amino acid sequence of SEQ ID NO:1, SEQ ID NO:2 or SEQ ID NO:3. In general, variant KAI peptide exhibits substantially the same or greater binding affinity than the KAI peptide of SEQ ID NO:1, SEQ ID NO:2 or SEQ ID NO:3, e.g., at least 0.75×, 0.8×, 0.9×, 1.0×, 1.25× or 1.5× the binding affinity. In certain embodiments, a KAI peptide or variant thereof has a $K_D$ value in the range of about 10 pM to about 1 pM, or more preferably about 10 pM to about 100 nM, or most preferably about 10 pM to about 10 nM.

In certain embodiments, the peptide is glycosylated, phosphorylated, sulfated, animated, carboxylated, or acetylated. For example, the C-terminal may be modified with amidation, addition of peptide alcohols and aldehydes, addition of esters, addition of p-nitroaniline and thioesters. The N-terminus and amino acid side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations, biotinylation, phosphorylation, sulfation, glycosylation, introduction of maleimido group, chelating moieties, chromophores and flurophores.

The KAI peptide and construct can be synthesized recombinantly using recombinant DNA techniques. Thus, in another aspect, the invention provides polynucleotides that encode the KAI peptide or construct of the invention. In a related aspect, the invention provides vectors, particularly expression vectors that harbor the polynucleotides encoding the KAI peptide or construct. In certain embodiments, the vector provides replication, transcription and/or translation regulatory sequences that facilitate recombinant synthesis of the KAI peptide or construct in eukaryotic or prokaryotic cells. Accordingly, the invention also provides host cells for recombinant expression of the KAI peptide or construct and methods of harvesting and purifying the KAI peptide or construct produced by the host cells. Production and purification of recombinant polypeptides is routine practice to one of skilled in the art. The KAI peptide or construct can be purified by any suitable methods known in the art including without limitation gel filtration and affinity purification. When the KAI peptide or construct of the invention is produced in the form of a fusion protein, the fusion moiety (or the epitope tag) can optionally be cleaved off using a protease before further analysis.

Alternatively, the KAI peptide or construct of the invention can be advantageously synthesized by any of the chemical synthesis techniques known in the art, particularly solid-phase synthesis techniques, for example, using commercially-available automated peptide synthesizers. See, for example, Stewart and Young, 1984, Solid Phase Peptide Synthesis, $2^{nd}$ ed., Pierce Chemical Co.; Tarn, et al. (1983) *J. Am. Chem. Soc.* 105:6442; Merrifield (1986) *Science* 232:341-347; and U.S. Pat. No. 5,424,398). Moreover, a combination of recombinant and chemical synthesis techniques is also contemplated.

In addition to a KAI peptide and construct, the present invention also encompasses a binding agent, e.g., an antibody, antibody fragment or aptamer, that specifically binds the KAI peptide of SEQ ID NO:1, a peptide of SEQ ID NO:2 or a peptide of SEQ ID NO:3, and does not bind to similar or related proteins, e.g., VEGFR1. The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments. An antibody can be chimeric, human, humanized and/or affinity matured. "Antibody fragments" include only a portion of an intact antibody, wherein the portion preferably retains at least one, preferably most or all, of the functions normally associated with that portion when present in an intact antibody, in particular binding to the KAI peptide.

KAI peptide binding agents can be produced by any suitable conventional method. For example, wherein the binding agent is an antibody, the instant KAI peptide is used to immunize, e.g., a mouse or rabbit, and monoclonal or polyclonal antibodies are generated by routine protocols. Fragments of such antibodies, e.g., Fab fragments, bispecific scFv fragments, Fd fragments and fragments produced by a Fab expression library, can also be generated and used as KAI peptide binding agents. A KAI peptide binding agent finds use in immunotherapy approaches for the treatment of disease as well as in the detection and purification of the KAI peptide.

Many diseases (characterized as "angiogenic diseases") are driven by persistent unregulated or abnormal angiogenesis resulting in excessive vascularity. For example, ocular neovascularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman (1986) *Cancer Res.* 46:467-473; Folkman (1989) *J. Natl. Cancer Inst.* 82:4-6). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites, such as the liver, the lung, and the bones (Weidner, et. Al. (1991) *N. Engl. J. Med.* 324(1):1-8).

Angiogenesis is believed to involve a complex interplay of molecules which both stimulate and inhibit the growth of endothelial cells, the primary cells of the capillary blood vessels. Under normal conditions, these molecules appear to maintain the microvasculature in a quiescent state (i.e., one of no capillary growth) for prolonged periods. When necessary, however (such as during wound repair), these cells can undergo rapid proliferation and turnover within a short period of time. Although angiogenesis is a highly regulated process under normal conditions, many conditions (characterized as "angiogenic diseases") are driven by persistent unregulated angiogenesis. Otherwise stated, unregulated angiogenesis may either cause a particular pathological condition directly or exacerbate an existing pathological condition.

As demonstrated herein, constructs containing the KAI peptide possess anti-angiogenic activity. As angiogenesis inhibitors, such peptides and constructs are useful in methods of inhibiting angiogenesis and treating a disease or condition in a subject characterized by excessive vascularity. In particular, the KAI peptide and construct of this invention are of use in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such peptides and constructs are also useful in treating solid tumors arising from hematopoietic malignancies such as leukemias (i.e., chloromas, plasmacytomas and the plaques and tumors of mycosis fungosides and cutaneous T-cell lymphoma/leukemia) as well as in the treatment of lymphomas (both Hodgkin's and non-Hodgkin's lymphomas). In addition, the KAI peptide and construct are useful in the prevention of metastases from the tumors described above either when used alone or in combination with radiotherapy and/or other chemotherapeutic agents.

Further uses of the KAI peptide and construct include the treatment and prophylaxis of autoimmune diseases such as rheumatoid, immune and degenerative arthritis; skin diseases such as psoriasis; blood vessel diseases such as hemagiomas, and capillary proliferation within atherosclerotic plaques; pulmonary fibrosis; Osler-Webber Syndrome; myocardial angiogenesis; asthma; plaque neovascularization; telangiectasia; hemophiliac joints; angiofibroma; ocular diseases and wound granulation. Other uses include the treatment of diseases characterized by excessive or abnormal stimulation of endothelial cells, including not limited to intestinal adhesions, Crohn's disease, atherosclerosis, scleroderma, and hypertrophic scars, i.e., keloids. Another use is as a birth control agent, by inhibiting ovulation and establishment of the placenta. The KAI peptide and construct of the invention are also useful in the treatment of diseases that have angiogenesis as a pathologic consequence such as cat scratch disease (*Rochele minutesalia quintosa*) and ulcers (*Helicobacter pylori*). The KAI peptide and construct of the invention are also useful to reduce bleeding by administration prior to surgery, especially for the treatment of resectable tumors.

Methods of treatment in accordance with this invention are carried out by administering to a subject, having a disease or condition characterized by excessive or abnormal vascularity, an effective amount of the KAI peptide, construct or pharmaceutical composition containing the same. As used herein, the term "administration" or "administering" refers to the process of delivering an agent to a patient. The process of administration can be varied, depending on the agent, or agents, and the desired effect. Administration can be accomplished by any means appropriate for the therapeutic agent, for example, by oral, parenteral, mucosal, pulmonary, topical, catheter-based, rectal, intracranial, intracerebroventricular, intracerebral, intravaginal or intrauterine delivery. Parenteral delivery can include for example, subcutaneous intravenous, intrauscular, intra-arterial, and injection into the tissue of an organ, particularly tumor tissue. Mucosal delivery can include, for example, intranasal delivery. Oral or intranasal delivery can include the administration of a propellant. Pulmonary delivery can include inhalation of the agent. Catheter-based delivery can include delivery by iontropheretic catheter-based delivery. Oral delivery can include delivery of a coated pill, or administration of a liquid by mouth. Administration can generally also include delivery with a pharmaceutically acceptable carrier, such as, for example, a buffer, a polypeptide, a peptide, a polysaccharide conjugate, a liposome, and/or a lipid. Gene therapy protocol is also considered an administration in which the therapeutic agent is a polynucleotide capable of accomplishing a therapeutic goal when expressed as a transcript or a peptide into the patient.

In certain embodiments, this invention provides a method for the treatment of an ocular disease or condition by administering an effective amount of a KAI peptide or construct containing the same to a subject in need of treatment. In particular, the KAI peptide or construct is of use in the treatment of ocular diseases such as retinopathy of prematurity, corneal graft rejection, retrolental fibroplasia, neovascular glaucoma, rubeosis, proliferative diabetic retinopathy, ischemic retinopathy, intraocular neovascularization, corneal neovascularization, retinal neovascularization, choroidal neovascularization, diabetic macular edema, diabetic retina ischemia, diabetic retinal edema, neovascular age-related macular degeneration (AMD), central retinal vein occlusion, branch retinal venin occlusion, retinitis pigmentosa, rubeosis iridis, visual impairment or vision loss (blindness) associated with angiogenesis, retinoblastoma, uveitis and corneal graft neovascularization, angiogenesis in the eye associated with infection or surgical intervention, and other abnormal neovascularization conditions of the eye.

In a particular embodiment, the invention provides a method for treating macular degeneration, including wet and dry macular degeneration, by administering an effective amount of a KAI peptide or construct containing the same to a subject in need of treatment. Wet macular degeneration occurs when abnormal blood vessels grow behind the macula. These vessels are fragile and can leak fluid and blood, which result in scarring of the macula and raise the potential for rapid, severe damage. Bruch's membrane breaks down, usually near drusen deposits. This is where new blood vessel growth, or neovascularization, occurs. Central vision can become distorted or lost entirely in a short period of time, sometimes within days.

"Treating" a subject having a disease or condition means accomplishing one or more of the following: (a) reducing the severity of the disease; (b) arresting the development of the disease or condition; (c) inhibiting worsening of the disease or condition; (d) limiting or preventing recurrence of the disease or condition in patients that have previously had the disease or condition; (e) causing regression of the disease or condition; (f) improving or eliminating the symptoms of the disease or condition; and (g) improving survival. While the subject can be any mammalian species, in certain embodiments, the subject being treated is a human and the disease or condition is an inflammatory disease, cancer, or retinal vasculopathy.

The extent of angiogenesis or vascularity can be determined using methods known in the art, such as those described herein, and can be done qualitatively or quantitatively. For example, molecular or cellular markers of cancer or tumor growth can be utilized. The extent of angiogenesis can also be determined by measuring the amount of endothelial cell proliferation or the extent of blood vessel growth within a biological sample. Such methods are of use both in identifying subjects in need of treatment and monitoring for therapeutic efficacy.

The KAI peptide or construct containing the same is ideally administered as a pharmaceutical composition containing the KAI peptide or construct and a pharmaceutically acceptable excipient. Suitable formulations are described in a number of sources which are well-known and readily available to those skilled in the art. For example, Remington: The Science and Practice of Pharmacy (Alfonso R. Gennaro, editor, 20$^{th}$ ed. Lippingcott Williams & Wilkins: Philadelphia, Pa., 2000) describes formulations which can be used in connection with the subject invention. The KAI peptide or construct can be incorporated in a conventional systemic dosage form, such as a tablet, capsule, soft gelatin capsule, elixir or injectable formulation. The dosage forms may also include the necessary physiologically acceptable excipient, carrier material, lubricant, buffer, surfactant, antibacterial, bulking agent (such as mannitol), antioxidants (ascorbic acid or sodium bisulfite) or the like. Acceptable formulation materials preferably are nontoxic to recipients at the dosages and concentrations employed.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as PLURONICS, PEG, sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; and/or pharmaceutical adjuvants.

The primary vehicle or excipient in a pharmaceutical composition may be either aqueous or nonaqueous in nature. For example, a suitable vehicle or excipient may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can include Tris buffer of about pH 7.0-8.5, or acetate buffer of about pH 4.0-5.5, which may further include sorbitol or a suitable substitute thereof. Pharmaceutical compositions may be prepared for storage by mixing the selected composition having the desired degree of purity with optional formulation agents in the form of a lyophilized cake or an aqueous solution. Further, the KAI peptide or construct may be formulated as a lyophilizate using appropriate excipients such as sucrose.

The KAI peptide or construct can be incorporated into pharmaceutical compositions suitable for ocular administration. Typically, the composition includes a pharmaceutically acceptable ophthalmic excipient. The ophthalmic excipient may be a buffer, tonicity adjuster, wetting agent, and/or an antioxidant. The buffer may be boric and/or phosphoric acid. The tonicity adjuster may provide an isotonic environment and may include sodium chloride, potassium chloride, magnesium chloride, and/or boric acid. Antioxidants include sodium metabisulfite and EDTA, for example. The antioxidants may be used to help stabilize the composition. Wetting agents, which include polyvinyl alcohol (PVA) and polysorbate 80, may allow the composition to spread over the eye. Other ophthalmic excipients include benzalkonium chloride (BAK), ethylenediaminetetraacetic acid (EDTA), purite, chlorobutanol, glycerin, dextran 70, propylene glycol, and polyethylene glycols, such as PEG-400. The ophthalmic excipient may be an ointment, such as mineral oil, white petrolatum, white ointment or lanolin. Similar to the aqueous vehicles, petrolatum and mineral oil may serve as vehicles in the ointment formulations to increase ocular contact time. These ingredients may help to form an occlusive film over the surface of the eyeball and improve the composition of the tear film by enhancing the mucin and aqueous layers. The ophthalmic excipient may provide mucin-like properties and/or decrease the loss of the aqueous layer due to evaporation. The ophthalmic excipient may function as a carrier, such as a pharmaceutically acceptable carrier.

Sterility typically will be maintained by conventional ophthalmic preservatives, e.g., chlorbutanol, benzalkonium chloride, cetylpyridinium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil. The following non-limiting examples are provided to further illustrate the present invention.

The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The formulations maybe presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

In one embodiment, the KAI peptide or construct is delivered in a sustained-release formulation, which provides extended release and extended half-life. Sustained-release systems suitable for use include, without limitation, diffusion-controlled, solvent-controlled and chemically-controlled systems. Diffusion controlled systems include, for example reservoir devices, in which the KAI peptide or construct is enclosed within a device such that release of the KAI peptide or construct is controlled by permeation through a diffusion barrier. Common reservoir devices include, for example, membranes, capsules, microcapsules, liposomes, and hollow fibers. Monolithic (matrix) devices are a second type of diffusion controlled system, wherein the KAI peptide or construct is dispersed or dissolved in a rate-controlling matrix (e.g., a polymer matrix). The KAI peptide or construct is homogeneously dispersed throughout a rate-controlling matrix and the rate of release is controlled by diffusion through the matrix. Polymers suitable for use in the monolithic matrix device include naturally occurring polymers, synthetic polymers and synthetically modified natural polymers, as well as polymer derivatives.

The KAI peptide or construct of this invention can also be administered in the form of a liposome delivery system, such as small unilamellar vesicles, large unilamellar vesicles and multilamellar vesicles. Liposomes can be formed from a variety of phospholipids, such as cholesterol, stearylamine or phosphatidylcholines. In certain embodiments, the formulation includes a liposome with a KAI peptide or construct associated with the surface of the liposome or encapsulated within the liposome. Preformed liposomes can be modified to associate with the KAI peptide or construct. For example, a cationic liposome associates through electrostatic interactions with the KAI peptide or construct. Alternatively, a KAI peptide or construct attached to a lipophilic compound, such as cholesterol, can be added to preformed liposomes whereby the cholesterol becomes associated with the liposomal membrane. Alternatively, the KAI peptide or construct can be associated with the liposome during the formulation of the liposome.

Solid lipid nanoparticles (SLNs) can also be used as alternative drug delivery systems to colloidal delivery systems such as lipid emulsions, liposomes, and polymeric nanoparticles. Various lipid matrices, surfactants, and other excipients used in formulation, preparation methods, sterilization and lyophilization of SLNs can be used. Entrapment efficiency of carrier and its effect on physical parameters, peptide release, and release mechanisms of various compositions are reviewed and discussed in Manjunath, et al. (2005) *Methods Find Exp Clin Pharmacol* 27(2):127.

Ocular administration of the KAI peptide or construct may be carried out using intraocular implants, intravitreal injections, systemic administration, topical application, nanoparticles, microparticles, eye drops, bioadhesive gels or fibrin sealant, polysaccharides to modulate the permeability of the epithelial cell barrier complex, peptide enhances corneal drug delivery, mucosal administration such as administration using a biovector polymer, aqueous opthamalic sprays and electrodynamic ocular spray treatment.

Therapeutically effective and optimal dosage ranges for the KAI peptide or construct can be determined using methods known in the art. The amount of the KAI peptide or construct which constitutes an "effective amount" or "therapeutically effective amount" may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect. Typical dosages range from about 0.1 µg/kg up to about 100 mg/kg body weight or more, depending on the factors mentioned above. In certain embodiments, the dosage may range from 0.1 µg/kg up to about 100 mg/kg, or 1 µg/kg up to about 100 mg/kg or 5 µg/kg up to about 100 mg/kg body weight. Pharmaceutical formulations that can be administered can include, e.g., 1-10,000 mg, 10-1000 mg, 50-900 mg, 100-800 mg, or 200-500 mg quantities of KAI peptide or construct.

To enhance treatment, the KAI peptide or construct disclosed herein can be used in combination with at least one additional therapeutic agent in order to treat a cancer, tumor or other proliferative disorder. The additional agents can be administered in combination or alternation with the KAI peptide or construct. The drugs can form part of the same composition, or be provided as a separate composition for administration at the same time or a different time. The second therapeutic agent can include, but is not limited to, retinoids, interferons, anti-neoplastic agents, radiation, antimitotic agents such as those which target cytoskeletal elements including microtubule modulators, podophylotoxins or vinca alkaloids, antimetabolite drugs, purine analogues, alkylating agents, drugs that target DNA such as the antracycline drugs, drugs that target topoisomerases, hormones and hormone agonists or antagonists, drugs that target signal transduction in tumor cells including antibody derivatives, drugs potentially affecting metastasis of tumors such as matrix metalloproteinase inhibitors, gene therapy and antisense agents, antibody therapeutics, corticosteroids, steroid analogues, anti-inflammatory drugs, and anti-emetic drugs. Examples of second therapeutic agents are disclosed in Table 2.

TABLE 2

| Second Therapeutic Agent | |
|---|---|
| Alkylating Agents | Nitrogen mustards: Melphalan, Cyclophosphamide, Ifosfamide |
| | Nitrosoureas |
| | Alkylsulfonates |
| | Ethyleneimines |
| | Triazene |
| | Methyl Hydrazines |
| | Platinum Coordination complexes: Cisplatin, Carboplatin, Oxaliplatin |
| Antimetabolites | Folate Antagonists: Methotrexate |
| | Purine antagonists |
| | Pyrimidine antagonists: 5-Fluorouracil, Cytarabibe |
| Plant Products | Vinca Alkaloids: Vincristine, Vinblastine |
| | Taxanes: Paclitaxel, Docetaxel |
| | Epipodophyllotoxins: Etoposide |
| | Camptothecins: Irinotecan |
| Microorganism Products | Antibiotics: Doxorubicin, Bleomycin |
| | Enzymes: L-Asparaginase |
| Miscellaneous | Hydroxyurea |
| | Imatinib Mesylate |
| | Rituximab |
| | Epirubicin |
| | Bortezomib |
| | Zoledronic Acid |
| | Geftinib |
| | Leucovorin |
| | Pamidronate |
| | Gemcitabine |
| Anti-VEGF | Bevacizumab |
| | Ranibizumab |
| | Lapatinib |
| | Sunitinib |
| | Sorafenib |
| | Axitinib |
| | Pazopanib |
| | Cediranib |
| | Pegaptanib |
| | Aflibercept |
| Hormones and Antagonists | Corticosteroids: Prednisone, Dexamethasone |
| | Estrogens: Ethinyloestradiol |
| | Anti-estrogens: Tamoxifen |
| | Progesterone derivative: Megestrol Acetate |
| | Androgen: Testosterone propionate |
| | Antiandrogen: Flutamide, Bicalutamide |
| | Aromatase inhibitor: Letrozole, Anastrazole |
| | 5-alpha reductase inhibitor: Finasteride |
| | GnRH Analogue: Leuprolide, Buserelin |
| | Growth Hormone, glucagon and insulin inhibitor: Octreotide |
| | Prostaglandins: Latanoprost, Bimatoprost, Travoprost, Unoprostone |

In addition, administration of the KAI peptide or construct for treating ocular diseases or condition may be combined with other procedures such as an implantable telescope, laser photocoagulation and macular translocation surgery.

Efficacy of a KAI peptide, construct or composition of this invention can be assessed using any suitable model of a disease or condition of interest. In particular, angiogenesis assays known in the art may be used. See, for example, US 2003/0077261, wherein rat aortic ring, bovine, mouse and human angiogenesis assays are described. Quantification of ring microvessel outgrowths as described, for example, in US 2003/0077261 may be used wherein ring cultures are photographed using a digital video camera linked to an OLYMPUS BX60 microscope and the outgrowth area is selectively measured and detected with the Image Pro Plus software. Endothelial Cell Migration Assays, described in US 2003/0077261 to Paris, et al. may be used where migration of human brain adult endothelial cells is evaluated using a modified Boyden chamber assay (BD BioCoat MATRIGEL Invasion Chamber). Nude Mouse Tumor Xenograft models as described, for example, in US 2003/0077261 to may be used, wherein A-549 (human lung adenocarcinoma) and U87-MG (human glioblastoma) cells are implanted into 8-week-old female nude mice. Tumors grown in the animals are measuring before, after and during treatment with KAI peptides or constructs. On the termination day of each in vivo antitumor study, tumors are extracted and microvessels are quantified.

The invention is described in greater detail by the following non-limiting examples.

Example 1: Materials and Methods

Antibodies and Reagents.

Antibodies against KIF13B (Sigma, St. Louis, Mo.), extracellular domain of VEGFR2 (Fitzgerald, Acton, Mass.), E-tag (Abcam, Cambridge, Mass.), von Willebrand factor based on analysis of VEGFR2-binding site in KIF13B (Millipore, Temecula, Calif.), and CD31 (Abcam) were used. Secondary antibodies were horseradish peroxidase-conjugated donkey anti-rabbit (Jackson ImmunoResearch, West Grove, Pa.), ALEXA-594-conjugated anti-rabbit (Life Technologies, Carlsbad, Calif.). WST-1 (Roche, Basel, Switzerland) and terminal deoxynucleotidyl transferase-mediated dUTP nick-end labeling (TUNEL) kit (Life Technologies) were also used.

Plasmids.

Human KIF13B cDNA was purchased from the Kazusa DNA Institute (Chiba, Japan). Truncated mutants were expressed in bacteria with His-tag and S-tag according to standard methods. Lentivirus and recombinant proteins were produced as described by Yamada, et al. ((2014) *J. Cell Sci.* 127:4518-30).

Peptides.

Peptides were custom synthesized by Pierce Biotechnology (Rockford, Ill.) at 95% purity, which was confirmed by reverse-phase high-performance liquid chromatography and mass spectrophotometry. Bulk peptides were aliquoted in glass vials (25 mg per vial) and kept in an excipient at −20° C. Once dissolved in sterile water in acidic condition (by adding <10% sterile acetic acid), pH was adjusted by adding sterile phosphate-buffered saline (PBS), and 10 mg/mL of the peptide in sterile PBS was aliquoted and kept at −20° C. freezer. Once thawed, peptide solutions were used within 2 to 3 days.

Cell Culture.

Human primary umbilical vein endothelial cells (HUVECs) (Lonza, Walkersville, N.J.) were maintained in EGM-2 (Lonza) supplemented with 10% FBS on 0.1% gelatin (Sigma)-coated culture dish. Passage 4~6 was used for experiments. Before stimulation with VEGF$^{165}$, HUVECs were serum starved in EBM-2 (Lonza) supplemented with 0.1% BSA (Sigma) for 2 hours. Recombinant human VEGF$^{165}$ (Miltenyi Biotech, Auburn, Calif.) was used at 50 ng/ml (2.2 nmol/l). HEK 293T/17 (ATCC), and human fibroblast Detroit 551 (ATCC, Manassas, Va.) were maintained in DMEM (Life Technologies) supplemented with 10% FBS. H460 cells were from ATCC and maintained in Dulbecco's modified Eagle's medium (Life Technologies) supplemented with 10% fetal bovine serum.

Angiogenesis Assays.

Collagen invasion assay was performed as previously described (Kang, et al. (2011) *J. Biol. Chem.* 286:42017-26). In vitro capillary network formation on MATRIGEL (BD Biosciences, San Jose, Calif.) and scratch wound healing assay were performed as previously described (Humtsoe, et al. (2010) *Mol. Cell Biol.* 30:1593-1606). Fibrin gel sprouting assay was performed as described by Nakatsu & Hughes ((2008) *Methods Enzymol.* 443:65-82). VEGF (2.2 nmol/L) stimulation was used for all in vitro angiogenesis assays. Transwell migration assay was performed as described by Kaplan, et al. ((2011) *Free Radical Res.* 45:1124-35) using VEGF (4.4 nmol/L), sphingosine-1-phosphate (S1P) (1 µmol/L), or basic fibroblast growth factor (bFGF) (50 ng/mL) in the presence or absence of kinesin-derived angiogenesis inhibitor (DUF2C5; residues 1238-1260 of KIF13B) at varying concentrations.

In Vitro Binding.

Truncated mutants of KIF13B were expressed in BL21 (DE3) or Rosetta-gami and purified as previously described (Yamada, et al. (2014) *J. Cell Sci.* 127:4518-30; Yamada, et al. (2007) *Biochemistry* 46:10039-45). Binding assay was performed with S-resin in 0.5% TRITON-X100 and 1% bovine serum albumin at 4° C. and analyzed by western blotting using anti-VEGFR2 antibody.

Proliferation, Viability, and Toxicity Assays.

VEGF-induced proliferation and viability of HUVECs were assessed by the WST-1 assay (Roche) as previously described (Cai, et al. (2006) *Microvasc. Res.* 71:20-31; Jones, eta l. (2005) *Br. J. Pharmacol.* 145:1093-102). HUVECs were cultured in reduced serum media (EBM2 supplemented with 0.1% fetal bovine serum and EC supplements, except VEGF, epidermal growth factor, insulin-like growth factor, and fibroblast growth factor). Then HUVECs were stimulated with VEGF (2.2 nmol/L), with and without DUF2C5 (1, 3, and 10 µmol/L), or negative control peptide (CT23, 3 µmol/L) for 48 hours to test VEGF-induced proliferation by WST-1 assay in a 96-well format. Viability of HUVECs was assessed with and without DUF2C5 (1, 3, and 10 µmol/L) after overnight incubation in growth medium. Apoptosis was measured by TUNEL assay (Invitrogen) after incubation with and without DUF2C5 in growth medium for 48 hours. As a positive control, 50 ng/mL of tumor necrosis factor (TNF)-α was also used in the apoptosis assay.

Endothelial Permeability Assay.

A VEGF-induced increase in endothelial permeability was assessed by leakage of fluorescein isothiocyanate-dextran across HUVEC monolayers. Transwells (with 0.4-µm-pore diameters) were coated with confluent HUVECs. After serum starvation, cells were pretreated with DUF2C5 or CT23 (10 µmol/L). Then the cells were stimulated with VEGF, and at various time points transendothelial fluorescein isothiocyanate-dextran permeability was measured using the fluorescence plate reader PHERASTAR (BMG Biotech, Cary, N.C.).

MATRIGEL Plug Vessel Formation Assay and Mouse Xenograft Model.

For the MATRIGEL plug assay used to assess vessel formation of mouse ECs, C57BL6 males (Jackson Laboratory) were used as previously described (Yang & Proweller (2011) *J. Biol. Chem.* 286:13741-53). MATRIGEL supplemented with 4.4 nmol/l VEGF, 50 ng/ml bFGF, 60 U heparin, and 0.8×10$^8$ IFU of lentivirus was injected subcutaneously into abdomen. Four days after injection, MATRIGEL was collected.

For mouse xenograft model, human lung carcinoma H460 (3×10$^6$ cells) s.c. was inoculated in the right flank of immunodeficient BALBc mice with severe combined immunodeficiency (Jackson Laboratory) under anesthesia as described (Eklund, et al. (2013) *Mol. Oncol.* 7:259-82; Yamada, et al. (2002) *Proc. Natl. Acad. Sci. USA.* 99:14098-103). After a palpable tumor had developed, mice received either 200 µL of PBS or peptide DUF2C5 (10 mg/kg dissolved in 200 µL of PBS) by i.v. injection via tail vein 3 times per week. Tumor size was measured three times per week using a caliper. After the treatment period, the tumor was fixed and paraffin embedded for immunohistologic analysis with anti-VEGFR2 antibody for assessment of tumor angiogenesis. The mice were housed in pathogen-free conditions in the University of Illinois Animal Care facility and treated in accordance with institutional guidelines.

Postnatal Retina Angiogenesis.

Neonatal C57B mice were given peptide (either DUF2C5 or CT23, 10 mg/kg dissolved in PBS) or PBS vehicle at the day of birth (postnasal day 0) and subsequent days (postnasal days 1 to 4) daily s.c. under eyelid as previously described (Chavala, et al. (2013) *J. Clin. Invest.* 123:4170-81). At postnatal day 6, the retina was isolated and stained with anti-CD31 antibody (Abcam) as previously described (Pitulescu, et al. (2010) *Nat. Protoc.* 5:1518-34).

Image Acquisition Protocol.

Microscopes used for this study were ZEISS confocal LSM 880 META with 63× oil immersion objective lens and ZEISS AXIOVERT phase-contrast microscope with PLAN-NEOFLUAR 5× objective, 20× objective lens, and 40× oil immersion objective lens. All fluorescence images were taken in the same conditions and settings for all samples in the same set of experiments.

Statistical Analysis.

The t-test was used for intergroup comparisons. To analyze more than two groups, one-way analysis of variance and post hoc Bonferroni multiple comparisons were performed with GraphPad Prism software version 5 (GraphPad Software, San Diego, Calif.).

Laser-Induced CNV.

Neovascular age-related macular degeneration (AMD) is characterized by growth of the blood vessels from the choroid, which penetrate through Bruch's membrane into the subretinal area. The mouse model of laser-induced choroidal neovascularization (CNV) is a well-established model of the exudative form of AMD. The disruption of Bruch's membrane by a laser beam promotes the growth of new choroidal vessels into the retina thus mimicking the pathological conditions of AMD.

Laser photocoagulation was induced using the image-guided laser system (Micron IV, Phoenix Research Laboratories, Pleasanton, Calif.) on C57B mice under anesthesia. Four laser burns at equal distance from the optic nerve was induced one by one in right eye by a green Argon laser pulse with a wavelength of 532 nm, a fixed diameter of 50 µm, duration of 70 ms, and power levels from 210-250 mW. Appearance of bubbles at the laser spot serves to indicate rupture of the Bruch's membrane and as confirmation of laser-induced CNV. This procedure was performed only at the right eye of each mouse.

Choroidal neovascularization was evaluated by ocular coherence tomography (OCT) and fluorescein angiography at day 7 and 14. Fluorescein angiography and OCT was performed for imaging the retinal vasculature, similar to the procedure routinely used clinically for patients. Fluorescein angiogram was performed via i.p injection of 0.5% fluorescein.

The experiments were terminated at day 14 after taking images of OCT and angiography. Eyes were taken, and the flat mount preparation of choroid/sclera was used for staining with ALEXA 594-labeled lectin from Bandeiraena simplicifolia (B4) for post-mortem analysis of CNV area. The area of vascular leakage and CNV was quantified using confocal image of CNV staining for lectin B4 using MetaMorph software. Data was plotted and analyzed statistically with Prism 6 (Graph Pad, San Diego Calif.).

Example 2: Identification of KIF13B-Derived Peptide-Inhibiting Angiogenesis

Using recombinant proteins, the binding sites on KIF13B mediating the interaction with VEGFR2 were identified. KIF13B has a motor, forkhead-associated, membrane-associated guanylate kinase-binding stalk, 2 domains of unknown function (DUFs) (DUF3694), and a proline-rich and cytoskeleton-associated protein glycine-rich domain. The DUFs were identified from amino acid sequence similarity on the Pfam database. It has been previously shown that both domains of DUF3694 directly bind recombinant VEGFR2 in vitro (Yamada, et al. (2007) Biochemistry 46:10039-45). To define the specific peptide sequence inhibiting VEGFR2 trafficking, further analysis of the second DUF3694 domain (DUF2, residues 1112-1281 of KIF13B) was carried out. This was based on stability of this domain and a sequence distinct from binding sites for other cargoes of KIF13B (Horiguchi, et al. (2006) J. Cell Biol. 174:425-436; Hanada, et al. (2000) J. Biol. Chem. 275:28774-2878). DUF2 was divided into 3 parts, DUF2A (residues 1111-1167), DUF2B (residues 1168-1216), and DUF2C (residues 1217-1281) and each part was expressed as a recombinant protein in bacteria. VEGFR2 was abundantly expressed in HUVECs; thus, cell lysate from HUVECs was incubated with these recombinant proteins on beads, and VEGFR2 binding was determined using the anti-VEGFR2 antibody. This analysis indicated that DUF2C specifically binds VEGFR2, whereas DUF2A and DUF2B and beads alone failed to bind.

To test the bioactivity of the truncated mutant of KIF13B, DUF2C was expressed by lentivirus vector in HUVECs. Expression of DUF2C was sufficient to reduce VEGF-induced capillary network formation in vitro, whereas vector-infected control HUVECs formed characteristic capillary networks in MATRIGEL plugs in the presence of VEGF. The collagen invasion system (Kang, et al. (2011) J. Biol. Chem. 286:42017-42026) was used as another angiogenesis assay to test the peptides. After infection with control lentivirus, FLAG-DUF2C, or FLAG-DUF2, HUVECs were seeded on collagen gels. Cell invasion in response to proangiogenic stimuli SIP and VEGF in the gel was monitored for up to 24 hours. Only the expression of DUF2C or the entire DUF2 sequence significantly reduced invasion of HUVECs into collagen gel, distance of invasion and number of lumen formed. Thickness of invading sprouts, however, was not different among the groups.

Figure 1:
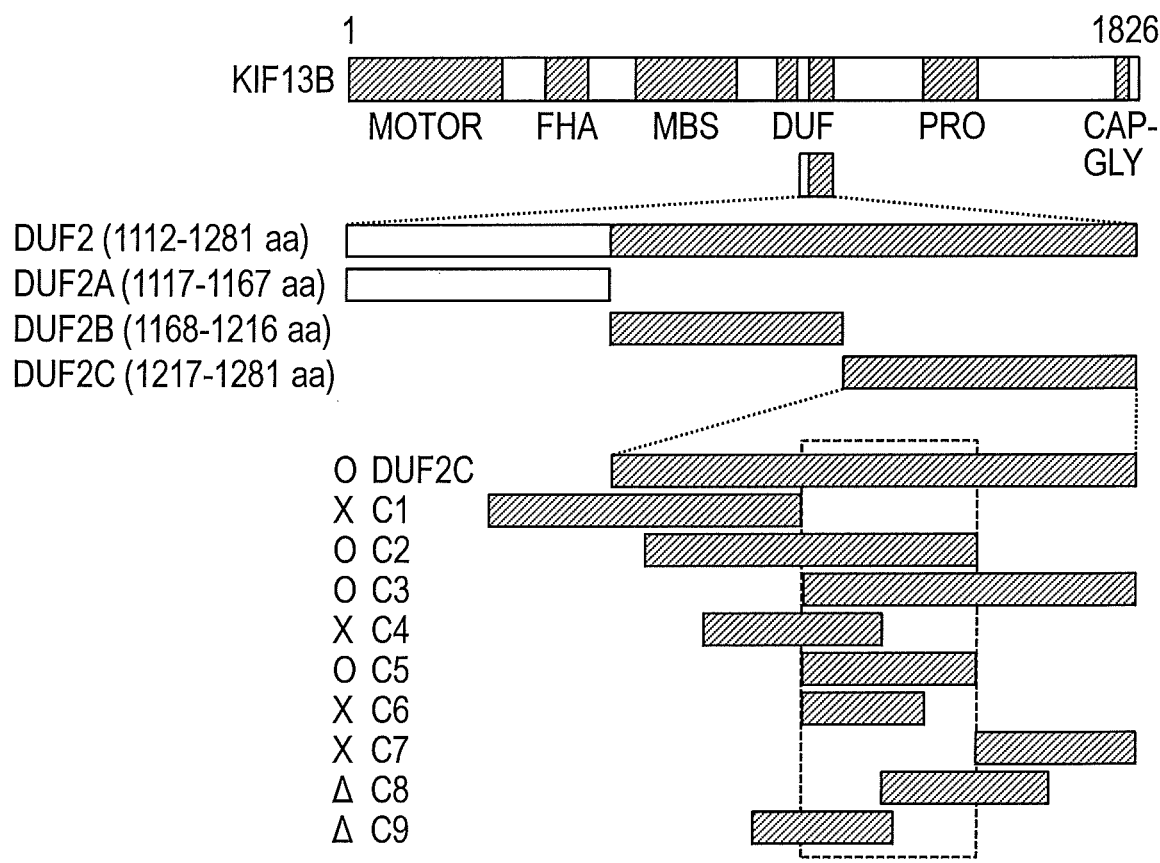
FIG. 1 shows a schematic of the domains of KIF13B and truncated domains used. Domains of unknown function (DUF) C1 [1202-1240 amino acids (aa)], C2 (1221-1260 aa), C3 (1241-1281 aa), C4 (1226-1251 aa), C5 (1238-1260 aa), C6 (1238-1254 aa), C7 (1261-1281 aa), C8 (1251-1268 aa), and C9 (1235-1252 aa) were expressed as recombinant proteins in bacteria and tested for binding to vascular endothelial growth factor receptor 2 (VEGFR2) by pull-down assay. O, X, and triangle indicate binding, no binding, and partial or unstable binding, respectively. Binding region is indicated as dashed box.

To identify the minimum binding site on VEGFR2, DUF2C was further truncated (DUF2C1-9) (FIG. 1). Among these, residues 1238 to 1260 of KIF13B (i.e., DUF2C5 or C5 peptide) included the core binding sequence as determined by pull-down binding assay with endogenous VEGFR2 from HUVEC lysates. Compared to C5, the truncated C6, C8, and C9 peptides exhibited partial or unstable binding with VEGFR2. Stability of the C5 peptide was attributed to the 4-6 C-terminal residues. Accordingly, replacing these C-terminal residues with another a peptide, one or more post-translational modifications, one or more non-natural amino acid residues, a macromolecule such as PEG, or a combination thereof, is expected to stabilize the KAI peptide.

Bioactivities in two-dimensional capillary network formation assay were assessed in HUVECs expressing KIF13B truncated mutants or vector controls. HUVECs were infected with lentiviruses encoding FLAG-C2, -C3, -C5, -C8, -C9, or vector. In addition, the C-terminus region of KIF13B (residues 1528 to 1826), which does not bind to bind to VEGFR2, was used as a negative control ($C_T$). Expression of truncated mutants C2, C3, and C5, which bind VEGFR2, significantly reduced VEGF-induced network formation, whereas vector-infected control HUVECs and $C_T$-expressed HUVECs formed capillary networks on MATRIGEL in the presence of VEGF. DUF2C8 and DUF2C9, which weakly bind VEGFR2, did not significantly reduce network formation.

Figure 2:
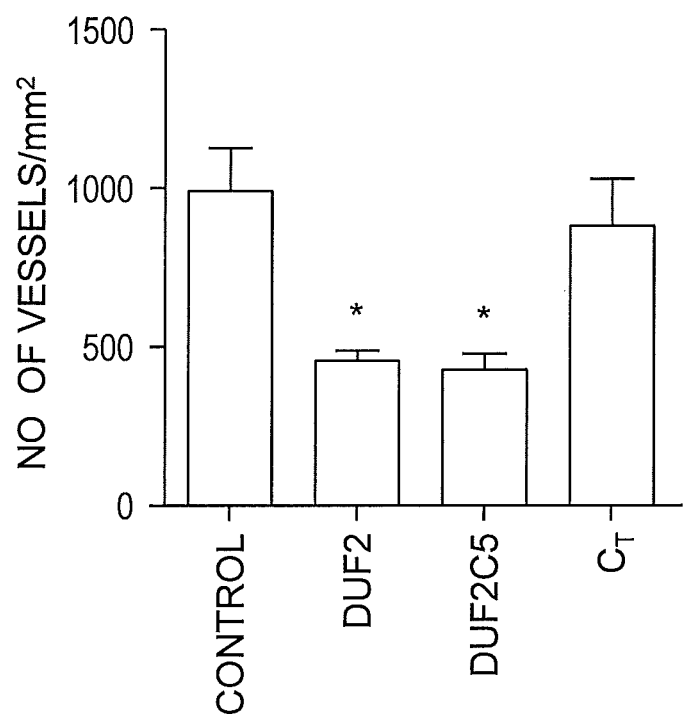
FIG. 2 shows that peptides derived from KIF13B inhibit vascular endothelial growth factor (VEGF)-induced angiogenesis. Hematoxylin and eosin staining of MATRIGEL plug was supplemented with 4.4 nmol/L VEGF, 50 ng/mL of basic fibroblast growth factor, 60 U of heparin, and $0.8 \times 10^8$ IFU lentivirus (vector control, DUF2, or DUF2C5, or $C_T$)

To address the role of KIF13B in mediating angiogenesis in vivo, the MATRIGEL plug assay was performed in mice using lentivirus expressing truncated mutants of KIF13B. High titer of lentivirus was injected with MATRIGEL s.c. into C57BL mice in the presence of VEGF, bFGF, and heparin. Interestingly, expression of DUF2C5 or full-length DUF2 significantly reduced the number of vessels, whereas vector control or expression of $C_T$ had no significant effect (FIG. 2). These results indicate that a peptide containing the minimum binding site of KIF13B for VEGFR2 inhibit angiogenesis in both the in vitro and in vivo angiogenesis assays.

Example 3: DUF2C5 Peptide Prevents Tumor Angiogenesis

Protein BLAST search revealed that DUF2C5 did not overlap with any other protein sequences. Using a competitive binding assay, it was determined whether DUF2C5 competed for binding of VEGFR2 with endogenous KIF13B in HUVECs. VEGFR2 co-immunoprecipitated with KIF13B in control cells, whereas pre-incubation with DUF2C5 prevented the interaction of VEGFR2 with KIF13B. Because interaction of KIF13B and VEGFR2 is necessary for trafficking of VEGFR2 to cell surface, the cell surface expression of VEGFR2 in the absence or presence of DUF2C5 was subsequently examined. Serum-starved HUVECs were pre-incubated with the DUF2C5 peptide (3, 10 µmol/L) or PBS control, and then the cells were stimulated with VEGF for the indicated times. Cell-surface localized VEGFR2 was stained by antibody against extracellular domain of VEGFR2 as described (Yamada, et al. (2007) Biochemistry 46:10039-45). In control cells, VEGFR2 was detected on the cell surface before VEGF stimulation, VEGFR2 disappeared at 1 hour after stimulation, and cell surface pool was restored by the transport of newly synthesized VEGFR2. Initial VEGFR2 cell-surface accumulation and internalization, however, were unaffected by pre-incubation of DUF2C5; that is, DUF2C5 only prevented the restoration of cell-surface VEGFR2 after VEGF stimulation.

To examine the specificity of DUF2C5, a negative control peptide was designed that does not bind to VEGFR2. Because the C-terminal region of KIF13B does not bind VEGFR2 (Yamada, et al. (2007) *Biochemistry* 46:10039-45), a C-terminal, 23-amino acid peptide termed CT23 (residues 1650 to 1672 of KIF13B) was synthesized. Initially, peptide interaction with VEGFR2 was confirmed using the pull-down assay. Biotin-DUF2C5 peptide immobilized on streptavidin beads pulled down VEGFR2 from HUVEC lysates, whereas beads alone or CT23 on beads did not interact with VEGFR2.

Next, EC uptake of the peptides by HUVECs was determined. Both DUF2C5 and CT23 were designed to have high pI (pH at which the molecules carry no net charge), pI 12.1 and 10.4, respectively; thus, in neutral pH, both peptides have a positive charge important for cellular uptake (Jones, et al. (2005) *Br. J. Pharmacol.* 145:1093-1102). DUF2C5 and CT23 were synthesized with a biotin-tag and visualized using streptavidin-ALEXA 418. After incubation with peptides for 2 hours, HUVECs were shown to internalize both the DUF2C5 and CT23 peptides as quantified by flow cytometry.

The effects of DUF2C5 on VEGF-induced proliferation were subsequently determined by the WST-1 assay. This analysis indicated that DUF2C5 inhibited VEGF-induced proliferation at concentrations of 3 and 10 μmol/L, whereas CT23 at 3 μmol/L had no effect. VEGF-induced increase in endothelial permeability was also determined using confluent HUVEC monolayers. This analysis showed that DUF2C5 inhibited VEGF-induced increase in permeability, whereas CT23 did not. HUVEC viability was also tested after incubation with DUF2C5 (1, 3, 10 μmol/L) for 24 hours using WST-1 assay. Even the highest DUF2C5 concentration of 10 μmol/L failed to alter cell viability. After incubation with DUF2C5 (10 μmol/L), PBS vehicle or TNF-α (50 ng/mL; as positive control), only TNF-α induced apoptosis.

EC migration in response to DUF2C5 was determined using the scratch wound healing assay. Control HUVECs (PBS vehicle or CT23) migrated and closed the wound in response to VEGF; however, VEGF-induced migration of HUVECs was markedly delayed in the presence of DUF2C5. The TRANSWELL migration assay was also employed to determine whether the inhibitory effect of DUF2C5 on EC migration was specific to VEGF. HUVECs were placed in the TRANSWELL chamber with or without DUF2C5 or CT23. DUF2C5 inhibited VEGF-induced EC migration but did not alter S1P- or bFGF-induced migration (FIG. 3). PBS and CT23 had no effect on EC migration induced by all stimuli.

Changes in VEGF-induced network formation assay were assessed in MATRIGEL plugs. DUF2C5 prevented VEGF-induced network formation in a concentration-dependent manner, whereas CT23 had no effect. VEGF-induced EC sprouting was also determined by 3-dimensional culture of HUVECs on beads (Nakatsu & Hughes (2008) *Methods Enzymol.* 443:65-82). Control cells and CT23 (1 μmol/L)-treated cells exhibited formation of long sprouts (e.g., approximately 13-16 sprouts) and multiple branching points (e.g., approximately 4-6 branches), whereas DUF2C5 (1 μmol/L) treatment markedly reduced the number of branching point structures (approximately 2 branches) and sprouts (approximately 6 sprouts) per bead.

To determine whether VEGFR2 trafficking regulated angiogenesis an in vivo cancer model, the tumor implantation mouse model was used (Eklund, et al. (2013) *Mol. Oncol.* 7:259-282). Studies were made using lung carcinoma because it depends on angiogenesis for tumor growth. Mice with severe combined immunodeficiency xenografted with human lung carcinoma H460 s.c. received either PBS or peptide DUF2C5 (10 mg/kg) by i.v. injection 3 times per week; this dosage is based on the in vitro testing dose regimen described herein. DUF2C5 inhibited tumor growth, whereas PBS-treated control tumor continued to grow (FIG. 4A). Blood vessels in tumor visualized by immunohistochemistry using anti-VEGFR2 and anti-von Willebrand factor antibodies revealed extensive vascularity in PBS-treated control tumor, whereas DUF2C5 treatment significantly decreased tumor vessel number (FIG. 4B). However, DUF2C5 did not directly affect viability of the cancer cells. TUNEL-positive tumor cell number, however, was increased in DUF2C5-treated mice (PBS, ~300 TUNEL-positive tumor cells/mm$^2$; DUF2C5, ~1750 TUNEL-positive tumor cells/mm$^2$).

To address whether DUF2C5 also reduced angiogenesis in another model, the effects of DUF2C5 were also tested in the model of postnatal retina angiogenesis. The peptides DUF2C5 or CT23 were injected daily from postnatal day 0 to day 4, and retina angiogenesis was determined at day 6. DUF2C5 in contrast to the anti-angiogenesis effect in tumors had no effect on developmental angiogenesis in retina.

Example 4: DUF2C5 Prevents Tumor Angiogenesis in Laser-Induced CNV

The laser induced CNV procedure was performed with C57B WT mice (7 weeks old). Treatment with DUF2C5 (0.5 μg, 2 μg, or 10 μg in 2 μL PBS) or PBS vehicle (2 μL) was administrated once via intravitreal injection after laser photocoagulation. OCT, fluorescein angiography, and staining with ALEXA 594-ILB4 were used to assess neovascularization. Compared to the PBS control, DUF2C5 treatment significantly inhibited neovascularization (FIG. 5A).

The effect of DUF2C5 as an eye drop was subsequently tested. Control peptide CT23, which does not inhibit angiogenesis, was used as a negative control. After laser-burn, mice were treated either control peptide (2 μg/eye) or DUF2C5 (2 μg/eye), daily. Neovascularization was assessed by OCT, fluorescein angiography, and staining with ILB4. Interestingly, daily treatment of DUF2C5 significantly inhibited neovascularization, whereas control peptide did not have any effect (FIG. 5B). Taken together, peptide DUF2C5 showed significant inhibition of AMD via intravitreal injection as well as eye drops.

Example 5: DUF2C5 Specificity

BLAST search analysis revealed that the peptide sequence of DUF2C5 is specific to KIF13B, and not found in any other proteins. Additionally, the sequence of DUF2C5 is highly conserved in mammalian KIF13B. DUF2C5 interacts with the kinase domain of VEGFR2 and does not interact with other receptors such as Tie2 and Par1. To further test the specificity of DUF2C5, pull-down of proteins was conducted using DUF2C5 or control peptide (CT23) immobilized on streptavidin beads followed by mass spec analysis of the binding proteins. This analysis detected the presence of KIF13B, VEGFR2, and co-receptor NRP1 (number of hits were 28, 11, and 5, respectively). Tie2, Par1, S1PR1, and FGFR were not found. Other cargo for KIF13B (e.g., CentA, hDlg) were also not found. Some receptor tyrosine kinases (i.e., PDGFRα, PDGFRβ, and EGFR) were also identified due to the similarity of the kinase domain (number of hits were 6, 5, and 1, respectively), whereas these kinases did not interact with the control peptide. The affinity of each receptor tyrosine kinase was subsequently tested via surface plasmon resonance (SPR) with BIACORE (UIC, RRC), using DUF2C5 and CT23 on an avidin-coated chip, and recombinant cytosolic domain of kinases (Fisher Scientific). VEGFR2 bound very tightly to DUF2C5 at $K_D$ value of 5.5±2.2 nM, whereas it did not bind to CT23. BIACORE also revealed that PDGFRβ showed very weak binding to DUF2C5 at negligible $K_D$, whereas PDGFRα and EGFR did not bind to DUF2C5. These data indicate a high degree of specificity of DUF2C5 for VEGFR2.

Example 6: Drug Delivery

Delivery of the DUF2C5 peptide was tested using synthesized peptide covalently conjugated with DY633 fluorescent probe (Pierce). DY633-DUF2C5 (10 mg/kg body weight), DY633-CT23 or DY633 alone were injected intravenous (i.v.) via tail vein in H460-tumor bearing SCID mice. After 1 hour, tumors were dissected and flash frozen in OCT. Cryosections of tumors were co-stained with vWF to visualize endothelial cells in tumors. This analysis demonstrated that both DY633-labeled peptides were found in vWF positive endothelial cells in tumors, whereas dye alone was not detected. These data indicate successful delivery of the DUF2C5 peptide into tumor sites.

Notably, cell penetration of the DUF2C5 peptide was attributed to the three N-terminal amino acid residues, Ser-Arg-Gly. Accordingly, replacing these residues with other charged residues (e.g., a cell penetrating peptide), a lipid, vitamin $B_{12}$, or a combination thereof is likewise expected to facilitate transport of the KAI peptide into cells.

Example 7: Truncation of DUF2C5 Peptide

To further define the KIF13B residues involved in binding to VEGFR2, truncations of the DUF2C5 peptide were tested for binding to VEGFR2 (Table 3) and compared to binding of DUF2C5 and peptides flanking this region (FIG. 1). Using a pull-down binding assay with endogenous VEGFR2 from HUVEC lysates, the results of this analysis indicated that a peptide having the sequence TPVDERLFLIVRVTVQ (SEQ ID NO:3) is sufficient for VEGFR2 binding. Notably, a cyclic version of the DUF2C5 peptide was also prepared and shown to bind to VEGFR2.

Example 8: KAI Orthologs

KIF13B has orthologs in a number of species including, but not limited to other non-mammals such as zebrafish and bird; and mammals including primate, canine, bovine and rodent. Orthologs of the *Homo sapiens* KAI peptide, TPVDERLFLIVRVTVQ (SEQ ID NO:3) are provided in Table 4.

TABLE 4

| Organism | Ortholog Sequence* | Sequence Identity[†] | SEQ ID NO: |
|---|---|---|---|
| Homo sapiens | TPVDERLFLIVRVTVQ[1] | 100% | 3 |
| Pan troglodytes | TPADERLFLIVRVTVQ[2] | 93.8% | 80 |
| Macaca mulatta | TPADERLFLIVRVTVQ[3] | 93.8% | 81 |
| Canis lupus | TPADERVYLIVRVTVQ[4] | 81.2% | 82 |
| Bos Taurus | TPVDERVFLIVRVTVQ[5] | 93.8% | 83 |
| Mus musculus | TPADERVFLILRVTVQ[6] | 81.2% | 84 |
| Rattus norvegicus | TPADERVFLILRVAVQ[7] | 75.0% | 85 |
| Gallus gallus | TAADERVYLIVRATVQ[8] | 68.8% | 86 |
| Danio rerio | TEANERVYLILRTTVR[9] | 50.0% | 87 |
| Aotus nancymaae | TPVDERLFLIVRVTVQ[10] | 100% | 3 |
| Gorilla gorilla | TPADERLFLIVRVTVQ[11] | 93.8% | 88 |
| Echinops telfairi | TPSDERLFLIVRVTVQ[12] | 93.8% | 89 |
| Hipposideros armiger | TPADERLFLIVRVTVQ[13] | 93.8% | 90 |
| Capra hircus | TPVDERVFLIVRVTVQ[14] | 93.8% | 91 |

TABLE 3

| Peptide | Sequence | SEQ ID NO: | Binding |
|---|---|---|---|
| DUF2C5 | SRGTPVDERLFLIVRVTVQLSHP | 71 | + |
| DUF2C5a | RGTPVDERLFLIVRVTVQLSHP | 72 | + |
| DUF2C5b | GTPVDERLFLIVRVTVQLSHP | 73 | + |
| DUF2C5c | RGTPVDERLFLIVRVTVQLS | 74 | + |
| DUF2C5d | RGTPVDERLFLIVRVTVQ | 75 | + |
| DUF2C6 | SRGTPVDERLFLIVRVT | 76 | − |
| DUF2C8 | VRVTVQLSHPADMQLVLR | 77 | − |
| DUF2C9 | PQLSRGTPVDERLFLIVR | 78 | − |
| DUF2C3 | TPVDERLFLIVRVTVQLSHPADMQLVLRKR . . . QGF | 79 | + |

TABLE 4-continued

| Organism | Ortholog Sequence* | Sequence Identity[†] | SEQ ID NO: |
|---|---|---|---|
| Rhinolophus sinicus | TPADERLFLIVRVTVQ[15] | 93.8% | 92 |
| Pteropus alecto | TPADERVFLIVRVTVQ[16] | 87.5% | 93 |

*Derived from GENBANK Accession No.: [1]NP_056069, [2]XP_001154346, [3]XP_002805344, [4]XP_534562, [5]XP_002689518, [6]NP_001074646, [7]NP_998791, [8]XP_004935945, [9]NP_001261000, [10]XP_021520839, [11]XP_004046891, [12]XP_004707777, [13]XP_019491694, [14]XP_017907342, [15]XP_019588675, and [16]XP_015440561. [†]Relative to Homo sapiens KAI peptide.

Notably, there is a high degree of sequence identity, i.e., approximately 75-100%, between the Homo sapiens KAI peptide of SEQ ID NO:3 and mammal peptide orthologs. Indeed, as described herein, the Homo sapiens DUF2C5 peptide (sharing 82.6% sequence identity with the corresponding mouse DUF2C5 peptide) was effective in inhibiting neovascularization in vivo in a mouse model of laser-induced choroidal neovascularization. Accordingly, this invention includes a construct including the Homo sapiens KAI peptide of TPVDERLFLIVRVTVQ (SEQ ID NO:3), as well as KAI peptide orthologs having the amino acid sequence Thr-Xaa$_1$-Xaa$_2$-Xaa$_3$-Glu-Arg-Xaa$_4$-Xaa$_5$-Leu-Ile-Xaa$_6$-Arg-Xaa$_7$-Xaa$_8$-Val-Xaa$_9$ (SEQ ID NO:1), wherein Xaa$_1$ is Pro, Ala or Glu; Xaa$_2$ is Val, Ala or Ser; Xaa$_3$ is Asp or Asn; Xaa$_4$ is Leu or Val; Xaa$_5$ is Phe or Tyr; Xaa$_6$ is Leu or Val; Xaa$_7$ is Val, Ala or Thr; Xaa$_8$ is Thr or Ala and Xaa$_9$ is Gln or Arg. In particular, this invention includes a construct including mammalian KAI peptide orthologs having the amino acid sequence Thr-Pro-Xaa$_1$-Asp-Glu-Arg-Xaa$_2$-Xaa$_3$-Leu-Ile-Xaa$_4$-Arg-Val-Xaa$_5$-Val-Xaa$_6$ (SEQ ID NO:2), wherein Xaa$_1$ is Val, Ala or Ser; Xaa$_2$ is Leu or Val; Xaa$_3$ is Phe or Tyr; Xaa$_4$ is Leu or Val; Xaa$_5$ is Thr or Ala; and Xaa$_6$ is Gln or Arg.

As with the Homo sapiens DUF2C5 peptide disclosed herein, KAI peptide orthologs can be modified with one or more carrier moieties and/or one or more stabilizing moieties. As such, the construct of this invention can have the structure of an exemplary construct listed in Table 5.

TABLE 5

| Exemplary Constructs | SEQ ID NO: |
|---|---|
| SRGTPVDERLFLIVRVTVQLSHP | 94 |
| SRGTPADERLFLIVRVTVQLSHP | 95 |
| SKGTPADERLFLIVRVTVQLSHP | 96 |
| SKGTPADERVYLIVRVTVQLSHP | 97 |
| SKGTPVDERVFLIVRVTVQLSHP | 98 |
| SKGTPADERVFLILRVTVQLSHP | 99 |
| SKGTPADERVFLILRVAVQLSHP | 100 |
| SKGTAADERVYLIVRATVQLSHP | 101 |
| NRVTEANERVYLILRTTVRLSHP | 102 |
| SKGTPVDERLFLIVRVTVQLSHP | 103 |
| SRGTPADERLFLIVRVTVQLSHP | 104 |
| SRGTPSDERLFLIVRVTVQLSHP | 105 |
| SKGTPADERLFLIVRVTVQLSHP | 106 |
| SKGTPVDERVFLIVRVTVQLSHP | 107 |
| SKGTPADERLFLIVRVTVQLSHP | 108 |
| SRGTPADERVFLIVRVTVQLSHP | 109 |
| Myr-TPVDERLFLIVRVTVQLSHP-NH$_2$ | 110 |
| Myr-TPADERVFLILRVTVQLSHP-NH$_2$ | 111 |
| Myr-TPADERVFLILRVAVQLSHP-NH$_2$ | 112 |
| SRGTPVDERLFLIVRVTVQLSHP-NH$_2$ | 113 |
| SKGTPADERVFLILRVTVQLSHP-NH$_2$ | 114 |
| SKGTPADERVFLILRVAVQLSHP-NH$_2$ | 115 |
| Myr-TPVDERLFLIVRVTVQ-NH$_2$ | 116 |
| Myr-TPADERVFLILRVTVQ-NH$_2$ | 117 |
| Myr-TPADERVFLILRVAVQ-NH$_2$ | 118 |
| SRGTPVDERLFLIVRVTVQ-PEG | 119 |
| SKGTPADERVFLILRVTVQ-PEG | 120 |
| SKGTPADERVFLILRVAVQ-PEG | 121 |
| RQIKIWFQNRRMKWKKTPVDERLFLIVRVTVQ-NH$_2$ | 122 |
| RQIKIWFQNRRMKWKKTPADERVFLILRVIVQ-NH$_2$ | 123 |
| RQIKIWFQNRRMKWKKTPADERVFLILRVAVQ-NH$_2$ | 124 |
| RQIKIWFQNRRMKWKKTPVDERLFLIVRVTVQ-PEG | 125 |
| RQIKIWFQNRRMKWKKTPADERVFLILRVTVQ-PEG | 126 |
| RQIKIWFQNRRMKWKKTPADERVFLILRVAVQ-PEG | 127 |
| SK(azido-B$_{12}$)GTPVDERLFLIVRVTVQLSHP-NH$_2$ | 128 |
| SK(azido-B$_{12}$)GTPADERVFLILRVTVQLSHP-NH$_2$ | 129 |
| SK(azido-B$_{12}$)GTPADERVFLILRVAVQLSHP-NH$_2$ | 130 |

*Myr, myristoylation; NH$_2$, amidation; PEG, PEGylation; azido-B$_{12}$, azidonation of lysine and Vitamin B$_{12}$ conjugation.

Accordingly, this invention includes a construct having the sequence:

(SEQ ID NO: 131)
(S/N)-(K/R)-(G/V)-T-(P/A/E)-(V/A/S)-(D/N)-ER-(L/V)-(F/Y)-LI-(V/L)-R-(V/A)-(T/A)-V-(Q/R)-LSHP;

(SEQ ID NO: 132)
S-(K/R)-GTP-(V/A/S)-DER-(L/V)-(F/Y)-LI-(V/L)-RV-(T/A)-VQLSHP;

(SEQ ID NO: 133)
myristoyl-TP-(A/V)-DER-(L/V)-FLI-(V/L)-RV-(T/A)-VQLSHP-NH$_2$;

(SEQ ID NO: 134)
myristoyl-TP-(A/V)-DER-(L/V)-FLI-(V/L)-RV-(T/A)-VQ-NH$_2$;

(SEQ ID NO: 135)
S-(K/R)-GTP-(V/A)-DER-(L/V)-FLI-(V/L)-RV-(T

```
<223> OTHER INFORMATION: Xaa denotes Leu or Val
<220> FEATURE:
<221> NAME/KEY: MISC_FEATURE
<222> LOCATION: (8)..(8)
<223> OTHER INFORMATION: Xaa denotes Phe or Tyr
<220> FEATURE:
<221> NAME/KEY: MISC_FEATURE
<222> LOCATION: (11)..(11)
<223> OTHER INFORMATION: Xaa denotes Leu or Val
<220> FEATURE:
<221> NAME/KEY: MISC_FEATURE
<222> LOCATION: (14)..(14)
<223> OTHER INFORMATION: Xaa denotes Thr or Ala
<220> FEATURE:
<221> NAME/KEY: MISC_FEATURE
<222> LOCATION: (16)..(16)
<223> OTHER INFORMATION: Xaa denotes Gln or Arg

<400> SEQUENCE: 2

Thr Pro Xaa Asp Glu Arg Xaa Xaa Leu Ile Xaa Arg Val Xaa Val Xaa
1               5                   10                  15

<210> SEQ ID NO 3
<211> LENGTH: 16
<212> TYPE: PRT
<213> ORGANISM: Homo sapiens

<400> SEQUENCE: 3

Thr Pro Val Asp Glu Arg Leu Phe Leu Ile Val Arg Val Thr Val Gln
1               5                   10                  15

<210> SEQ ID NO 4
<211> LENGTH: 16
<212> TYPE: PRT
<213> ORGANISM: Artificial sequence
<220> FEATURE:
<223> OTHER INFORMATION: Synthetic peptide

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 10
<212> TYPE: PRT
<213> ORGANISM: Artificial sequence
<220> FEATURE:
<223> OTHER INFORMATION: Synthetic peptide

<400> SEQUENCE: 5

Phe Arg Glu Lys Leu Ala Tyr Ile Ala Pro
1               5                   10

<210> SEQ ID NO 6
<211> LENGTH: 16
<212> TYPE: PRT
<213> ORGANISM: Artificial sequence
<220> FEATURE:
<223> OTHER INFORMATION: Synthetic peptide

<400> SEQUENCE: 6

Arg Lys Lys Arg Arg Arg Glu Ser Arg Lys Lys Arg Arg Glu Ser
1               5                   10                  15

<210> SEQ ID NO 7
<211> LENGTH: 17
<212> TYPE: PRT
<213> ORGANISM: Artificial sequence
<220> FEATURE:
```

<223> OTHER INFORMATION: Synthetic peptide

<400> SEQUENCE: 7

Gly Arg Pro Arg Glu Ser Gly Lys Lys Arg Lys Arg Lys Arg Leu Lys
1               5                   10                  15

Pro

<210> SEQ ID NO 8
<211> LENGTH: 15
<212> TYPE: PRT
<213> ORGANISM: Artificial sequence
<220> FEATURE:
<223> OTHER INFORMATION: Synthetic peptide

<400> SEQUENCE: 8

Gly Lys Arg Lys Lys Lys Gly Lys Leu Gly Lys Lys Arg Asp Pro
1               5                   10                  15

<210> SEQ ID NO 9
<211> LENGTH: 17
<212> TYPE: PRT
<213> ORGANISM: Artificial sequence
<220> FEATURE:
<223> OTHER INFORMATION: Synthetic peptide

<400> SEQUENCE: 9

Gly Lys Arg Lys Lys Lys Gly Lys Leu Gly Lys Lys Arg Pro Arg Ser
1               5                   10                  15

Arg

<210> SEQ ID NO 10
<211> LENGTH: 18
<212> TYPE: PRT
<213> ORGANISM: Artificial sequence
<220> FEATURE:
<223> OTHER INFORMATION: Synthetic peptide

<400> SEQUENCE: 10

Arg Lys Lys Arg Arg Arg Glu Ser Arg Ala Arg Arg Ser Pro Arg
1               5                   10                  15

His Leu

<210> SEQ ID NO 11
<211> LENGTH: 19
<212> TYPE: PRT
<213> ORGANISM: Artificial sequence
<220> FEATURE:
<223> OTHER INFORMATION: Synthetic peptide

<400> SEQUENCE: 11

Ser Arg Arg Ala Arg Arg Ser Pro Arg Glu Ser Gly Lys Lys Arg Lys
1               5                   10                  15

Arg Lys Arg

<210> SEQ ID NO 12
<211> LENGTH: 19
<212> TYPE: PRT
<213> ORGANISM: Artificial sequence
<220> FEATURE:
<223> OTHER INFORMATION: Synthetic peptide

<400> SEQUENCE: 12

Val Lys Arg Gly Leu Lys Leu Arg His Val Arg Pro Arg Val Thr Arg
1               5                   10                  15

Met Asp Val

<210> SEQ ID NO 13
<211> LENGTH: 18
<212> TYPE: PRT
<213> ORGANISM: Artificial sequence
<220> FEATURE:
<223> OTHER INFORMATION: Synthetic peptide

<400> SEQUENCE: 13

Val Lys Arg Gly Leu Lys Leu Arg His Val Arg Pro Arg Val Thr Arg
1               5                   10                  15

Asp Val

<210> SEQ ID NO 14
<211> LENGTH: 14
<212> TYPE: PRT
<213> ORGANISM: Artificial sequence
<220> FEATURE:
<223> OTHER INFORMATION: Synthetic peptide

<400> SEQUENCE: 14

Ser Arg Arg Ala Arg Arg Ser Pro Arg His Leu Gly Ser Gly
1               5                   10

<210> SEQ ID NO 15
<211> LENGTH: 16
<212> TYPE: PRT
<213> ORGANISM: Artificial sequence
<220> FEATURE:
<223> OTHER INFORMATION: Synthetic peptide

<400> SEQUENCE: 15

Leu Arg Arg Glu Arg Gln Ser Arg Leu Arg Arg Glu Arg Gln Ser Arg
1               5                   10                  15

<210> SEQ ID NO 16
<211> LENGTH: 22
<212> TYPE: PRT
<213> ORGANISM: Artificial sequence
<220> FEATURE:
<223> OTHER INFORMATION: Synthetic peptide

<400> SEQUENCE: 16

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 17
<211> LENGTH: 8
<212> TYPE: PRT
<213> ORGANISM: Artificial sequence
<220> FEATURE:
<223> OTHER INFORMATION: Synthetic peptide

<400> SEQUENCE: 17

Lys Arg Gly Leu Lys Leu Arg His
1               5

<210> SEQ ID NO 18
<211> LENGTH: 21
<212> TYPE: PRT
<213> ORGANISM: Artificial sequence
<220> FEATURE:

<223> OTHER INFORMATION: Synthetic peptide

<400> SEQUENCE: 18

Thr Arg Ser Ser Arg Ala Gly Leu Gln Phe Pro Val Gly Arg Val His
1               5                   10                  15

Arg Leu Leu Arg Lys
            20

<210> SEQ ID NO 19
<211> LENGTH: 30
<212> TYPE: PRT
<213> ORGANISM: Artificial sequence
<220> FEATURE:
<223> OTHER INFORMATION: Synthetic peptide

<400> SEQUENCE: 19

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 20
<211> LENGTH: 21
<212> TYPE: PRT
<213> ORGANISM: Artificial sequence
<220> FEATURE:
<223> OTHER INFORMATION: Synthetic peptide

<400> SEQUENCE: 20

Lys Gly Ser Trp Tyr Ser Met Arg Lys Met Ser Met Lys Ile Arg Pro
1               5                   10                  15

Phe Phe Pro Gln Gln
            20

<210> SEQ ID NO 21
<211> LENGTH: 20
<212> TYPE: PRT
<213> ORGANISM: Artificial sequence
<220> FEATURE:
<223> OTHER INFORMATION: Synthetic peptide

<400> SEQUENCE: 21

Lys Thr Arg Tyr Tyr Ser Met Lys Lys Thr Thr Met Lys Ile Ile Pro
1               5                   10                  15

Phe Asn Arg Leu
            20

<210> SEQ ID NO 22
<211> LENGTH: 20
<212> TYPE: PRT
<213> ORGANISM: Artificial sequence
<220> FEATURE:
<223> OTHER INFORMATION: Synthetic peptide

<400> SEQUENCE: 22

Arg Gly Ala Asp Tyr Ser Leu Arg Ala Val Arg Met Lys Ile Arg Pro
1               5                   10                  15

Leu Val Thr Gln
            20

<210> SEQ ID NO 23
<211> LENGTH: 24
<212> TYPE: PRT
<213> ORGANISM: Artificial sequence

```
<220> FEATURE:
<223> OTHER INFORMATION: Synthetic peptide

<400> SEQUENCE: 23

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 24
<211> LENGTH: 12
<212> TYPE: PRT
<213> ORGANISM: Artificial sequence
<220> FEATURE:
<223> OTHER INFORMATION: Synthetic peptide

<400> SEQUENCE: 24

Thr Ser Pro Leu Asn Ile His Asn Gly Gln Lys Leu
1               5                   10

<210> SEQ ID NO 25
<211> LENGTH: 12
<212> TYPE: PRT
<213> ORGANISM: Artificial sequence
<220> FEATURE:
<223> OTHER INFORMATION: Synthetic peptide

<400> SEQUENCE: 25

Asn Ser Ala Ala Phe Glu Asp Leu Arg Val Leu Ser
1               5                   10

<210> SEQ ID NO 26
<211> LENGTH: 30
<212> TYPE: PRT
<213> ORGANISM: Artificial sequence
<220> FEATURE:
<223> OTHER INFORMATION: Synthetic peptide

<400> SEQUENCE: 26

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 27
<211> LENGTH: 16
<212> TYPE: PRT
<213> ORGANISM: Artificial sequence
<220> FEATURE:
<223> OTHER INFORMATION: Synthetic peptide

<400> SEQUENCE: 27

Ala Ala Val Ala Leu Leu Pro Ala Val Leu Leu Ala Leu Leu Ala Pro
1               5                   10                  15

<210> SEQ ID NO 28
<211> LENGTH: 10
<212> TYPE: PRT
<213> ORGANISM: Artificial sequence
<220> FEATURE:
<223> OTHER INFORMATION: Synthetic peptide

<400> SEQUENCE: 28

Val Pro Met Leu Lys Pro Met Leu Lys Glu
1               5                   10
```

<210> SEQ ID NO 29
<211> LENGTH: 18
<212> TYPE: PRT
<213> ORGANISM: Artificial sequence
<220> FEATURE:
<223> OTHER INFORMATION: Synthetic peptide

<400> SEQUENCE: 29

Lys Leu Ala Leu Lys Leu Ala Leu Lys Ala Leu Lys Ala Ala Leu Lys
1               5                   10                  15

Leu Ala

<210> SEQ ID NO 30
<211> LENGTH: 27
<212> TYPE: PRT
<213> ORGANISM: Artificial sequence
<220> FEATURE:
<223> OTHER INFORMATION: Synthetic peptide

<400> SEQUENCE: 30

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 31
<211> LENGTH: 16
<212> TYPE: PRT
<213> ORGANISM: Artificial sequence
<220> FEATURE:
<223> OTHER INFORMATION: Synthetic peptide

<400> SEQUENCE: 31

Ala Ala Val Ala Leu Leu Pro Ala Val Leu Leu Ala Leu Leu Ala Pro
1               5                   10                  15

<210> SEQ ID NO 32
<211> LENGTH: 9
<212> TYPE: PRT
<213> ORGANISM: Artificial sequence
<220> FEATURE:
<223> OTHER INFORMATION: Synthetic peptide

<400> SEQUENCE: 32

Val Gln Arg Lys Arg Gln Lys Leu Met
1               5

<210> SEQ ID NO 33
<211> LENGTH: 21
<212> TYPE: PRT
<213> ORGANISM: Artificial sequence
<220> FEATURE:
<223> OTHER INFORMATION: Synthetic peptide

<400> SEQUENCE: 33

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 34
<211> LENGTH: 15
<212> TYPE: PRT
<213> ORGANISM: Artificial sequence
<220> FEATURE:

```
<223> OTHER INFORMATION: Synthetic peptide

<400> SEQUENCE: 34

Ser Asp Leu Trp Glu Met Met Val Ser Leu Ala Cys Gln Tyr
1               5                   10                  15

<210> SEQ ID NO 35
<211> LENGTH: 16
<212> TYPE: PRT
<213> ORGANISM: Artificial sequence
<220> FEATURE:
<223> OTHER INFORMATION: Synthetic peptide

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 7
<212> TYPE: PRT
<213> ORGANISM: Artificial sequence
<220> FEATURE:
<223> OTHER INFORMATION: Synthetic peptide

<400> SEQUENCE: 36

Arg Arg Met Lys Trp Lys Lys
1               5

<210> SEQ ID NO 37
<211> LENGTH: 7
<212> TYPE: PRT
<213> ORGANISM: Artificial sequence
<220> FEATURE:
<223> OTHER INFORMATION: Synthetic peptide

<400> SEQUENCE: 37

Arg Arg Arg Arg Arg Arg Arg
1               5

<210> SEQ ID NO 38
<211> LENGTH: 9
<212> TYPE: PRT
<213> ORGANISM: Artificial sequence
<220> FEATURE:
<223> OTHER INFORMATION: Synthetic peptide

<400> SEQUENCE: 38

Arg Arg Arg Arg Arg Arg Arg Arg Arg
1               5

<210> SEQ ID NO 39
<211> LENGTH: 16
<212> TYPE: PRT
<213> ORGANISM: Artificial sequence
<220> FEATURE:
<223> OTHER INFORMATION: Synthetic peptide

<400> SEQUENCE: 39

Arg Val Ile Arg Val Trp Phe Gln Asn Lys Arg Cys Lys Asp Lys Lys
1               5                   10                  15

<210> SEQ ID NO 40
<211> LENGTH: 28
<212> TYPE: PRT
<213> ORGANISM: Artificial sequence
<220> FEATURE:
<223> OTHER INFORMATION: Synthetic peptide
```

-continued

<400> SEQUENCE: 40

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 41
<211> LENGTH: 18
<212> TYPE: PRT
<213> ORGANISM: Artificial sequence
<220> FEATURE:
<223> OTHER INFORMATION: Synthetic peptide

<400> SEQUENCE: 41

Leu Leu Ile Ile Leu Arg Arg Arg Ile Arg Lys Gln Ala His Ala His
1               5                   10                  15

Ser Lys

<210> SEQ ID NO 42
<211> LENGTH: 9
<212> TYPE: PRT
<213> ORGANISM: Artificial sequence
<220> FEATURE:
<223> OTHER INFORMATION: Synthetic peptide

<400> SEQUENCE: 42

Arg Arg Trp Trp Arg Arg Trp Arg Arg
1               5

<210> SEQ ID NO 43
<211> LENGTH: 18
<212> TYPE: PRT
<213> ORGANISM: Artificial sequence
<220> FEATURE:
<223> OTHER INFORMATION: Synthetic peptide

<400> SEQUENCE: 43

Val Arg Leu Pro Pro Pro Val Arg Leu Pro Pro Pro Val Arg Leu Pro
1               5                   10                  15

Pro Pro

<210> SEQ ID NO 44
<211> LENGTH: 7
<212> TYPE: PRT
<213> ORGANISM: Artificial sequence
<220> FEATURE:
<223> OTHER INFORMATION: Synthetic peptide

<400> SEQUENCE: 44

Pro Lys Lys Lys Arg Lys Val
1               5

<210> SEQ ID NO 45
<211> LENGTH: 18
<212> TYPE: PRT
<213> ORGANISM: Artificial sequence
<220> FEATURE:
<223> OTHER INFORMATION: Synthetic peptide

<400> SEQUENCE: 45

Arg Gly Gly Arg Leu Ser Tyr Ser Arg Arg Arg Phe Ser Thr Ser Thr
1               5                   10                  15

Gly Arg

<210> SEQ ID NO 46
<211> LENGTH: 10
<212> TYPE: PRT
<213> ORGANISM: Artificial sequence
<220> FEATURE:
<223> OTHER INFORMATION: Synthetic peptide

<400> SEQUENCE: 46

Arg Arg Leu Ser Tyr Ser Arg Arg Arg Phe
1               5                   10

<210> SEQ ID NO 47
<211> LENGTH: 17
<212> TYPE: PRT
<213> ORGANISM: Artificial sequence
<220> FEATURE:
<223> OTHER INFORMATION: Synthetic peptide

<400> SEQUENCE: 47

Ala Trp Ser Phe Arg Val Ser Tyr Arg Gly Ile Ser Tyr Arg Arg Ser
1               5                   10                  15

Arg

<210> SEQ ID NO 48
<211> LENGTH: 14
<212> TYPE: PRT
<213> ORGANISM: Artificial sequence
<220> FEATURE:
<223> OTHER INFORMATION: Synthetic peptide

<400> SEQUENCE: 48

Tyr Gly Arg Lys Lys Arg Arg Gln Arg Arg Pro Pro Gln
1               5                   10

<210> SEQ ID NO 49
<211> LENGTH: 11
<212> TYPE: PRT
<213> ORGANISM: Artificial sequence
<220> FEATURE:
<223> OTHER INFORMATION: Synthetic peptide

<400> SEQUENCE: 49

Tyr Gly Arg Lys Lys Arg Arg Gln Arg Arg
1               5                   10

<210> SEQ ID NO 50
<211> LENGTH: 9
<212> TYPE: PRT
<213> ORGANISM: Artificial sequence
<220> FEATURE:
<223> OTHER INFORMATION: Synthetic peptide

<400> SEQUENCE: 50

Arg Lys Lys Arg Arg Gln Arg Arg
1               5

<210> SEQ ID NO 51
<211> LENGTH: 13
<212> TYPE: PRT
<213> ORGANISM: Artificial sequence
<220> FEATURE:
<223> OTHER INFORMATION: Synthetic peptide

<400> SEQUENCE: 51

Gly Arg Lys Lys Arg Arg Gln Arg Arg Arg Pro Pro Gln

<210> SEQ ID NO 52
<211> LENGTH: 27
<212> TYPE: PRT
<213> ORGANISM: Artificial sequence
<220> FEATURE:
<223> OTHER INFORMATION: Synthetic peptide

<400> SEQUENCE: 52

Gly Trp Thr Leu Asn Ser Ala Gly Tyr Leu Leu Gly Lys Ile Asn Leu
1               5                   10                  15
Lys Ala Leu Ala Ala Leu Ala Lys Lys Thr Leu
            20                  25

<210> SEQ ID NO 53
<211> LENGTH: 21
<212> TYPE: PRT
<213> ORGANISM: Artificial sequence
<220> FEATURE:
<223> OTHER INFORMATION: Synthetic peptide

<400> SEQUENCE: 53

Ala Gly Tyr Leu Leu Gly Lys Ile Asn Leu Lys Ala Leu Ala Ala Leu
1               5                   10                  15
Ala Lys Lys Ile Leu
            20

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Gly Trp Thr Leu Asn Ser Ala Gly Tyr Leu Leu Gly
1               5                   10

<210> SEQ ID NO 55
<211> LENGTH: 14
<212> TYPE: PRT
<213> ORGANISM: Artificial sequence
<220> FEATURE:
<223> OTHER INFORMATION: Synthetic peptide

<400> SEQUENCE: 55

Ile Asn Leu Lys Ala Leu Ala Ala Leu Ala Lys Lys Thr Leu
1               5                   10

<210> SEQ ID NO 56
<211> LENGTH: 34
<212> TYPE: PRT
<213> ORGANISM: Artificial sequence
<220> FEATURE:
<223> OTHER INFORMATION: Synthetic peptide

<400> SEQUENCE: 56

Asp Ala Ala Thr Ala Thr Arg Gly Arg Ser Ala Ala Ser Arg Pro Thr
1               5                   10                  15
Glu Arg Pro Arg Ala Pro Ala Arg Ser Ala Ser Arg Pro Arg Pro
            20                  25                  30
Val Asp

-continued

```
<210> SEQ ID NO 57
<211> LENGTH: 26
<212> TYPE: PRT
<213> ORGANISM: Artificial sequence
<220> FEATURE:
<223> OTHER INFORMATION: Synthetic peptide

<400> SEQUENCE: 57

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 58
<211> LENGTH: 3
<212> TYPE: PRT
<213> ORGANISM: Artificial sequence
<220> FEATURE:
<223> OTHER INFORMATION: Synthetic peptide

<400> SEQUENCE: 58

Ser Arg Gly
1

<210> SEQ ID NO 59
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Ser or Asn
<220> FEATURE:
<221> NAME/KEY: MISC_FEATURE
<222> LOCATION: (2)..(2)
<223> OTHER INFORMATION: Xaa denotes Lys or Arg
<220> FEATURE:
<221> NAME/KEY: MISC_FEATURE
<222> LOCATION: (3)..(3)
<223> OTHER INFORMATION: Xaa denotes Gal or Val

<400> SEQUENCE: 59

Xaa Xaa Xaa
1

<210> SEQ ID NO 60
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Lys or Arg

<400> SEQUENCE: 60

Ser Xaa Gly
1

<210> SEQ ID NO 61
<211> LENGTH: 4
<212> TYPE: PRT
<213> ORGANISM: Artificial sequence
<220> FEATURE:
<223> OTHER INFORMATION: Synthetic peptide

<400> SEQUENCE: 61
```

Leu Ser His Pro
1

<210> SEQ ID NO 62
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Gln or Arg

<400> SEQUENCE: 62

Leu Ser His Pro Ala Asp
1               5

<210> SEQ ID NO 63
<211> LENGTH: 5
<212> TYPE: PRT
<213> ORGANISM: Artificial sequence
<220> FEATURE:
<223> OTHER INFORMATION: Synthetic peptide

<400> SEQUENCE: 63

Gly Ser Gly Gly Ser
1               5

<210> SEQ ID NO 64
<211> LENGTH: 4
<212> TYPE: PRT
<213> ORGANISM: Artificial sequence
<220> FEATURE:
<223> OTHER INFORMATION: Synthetic peptide

<400> SEQUENCE: 64

Gly Gly Gly Ser
1

<210> SEQ ID NO 65
<211> LENGTH: 4
<212> TYPE: PRT
<213> ORGANISM: Artificial sequence
<220> FEATURE:
<223> OTHER INFORMATION: Synthetic peptide

<400> SEQUENCE: 65

Gly Gly Ser Gly
1

<210> SEQ ID NO 66
<211> LENGTH: 5
<212> TYPE: PRT
<213> ORGANISM: Artificial sequence
<220> FEATURE:
<223> OTHER INFORMATION: Synthetic peptide

<400> SEQUENCE: 66

Gly Gly Ser Gly Gly
1               5

<210> SEQ ID NO 67
<211> LENGTH: 5
<212> TYPE: PRT
<213> ORGANISM: Artificial sequence
<220> FEATURE:

```
<223> OTHER INFORMATION: Synthetic peptide

<400> SEQUENCE: 67

Gly Ser Gly Ser Gly
1               5

<210> SEQ ID NO 68
<211> LENGTH: 5
<212> TYPE: PRT
<213> ORGANISM: Artificial sequence
<220> FEATURE:
<223> OTHER INFORMATION: Synthetic peptide

<400> SEQUENCE: 68

Gly Ser Gly Gly Gly
1               5

<210> SEQ ID NO 69
<211> LENGTH: 5
<212> TYPE: PRT
<213> ORGANISM: Artificial sequence
<220> FEATURE:
<223> OTHER INFORMATION: Synthetic peptide

<400> SEQUENCE: 69

Gly Gly Gly Ser Gly
1               5

<210> SEQ ID NO 70
<211> LENGTH: 5
<212> TYPE: PRT
<213> ORGANISM: Artificial sequence
<220> FEATURE:
<223> OTHER INFORMATION: Synthetic peptide

<400> SEQUENCE: 70

Gly Ser Ser Ser Gly
1               5

<210> SEQ ID NO 71
<211> LENGTH: 23
<212> TYPE: PRT
<213> ORGANISM: Homo sapiens

<400> SEQUENCE: 71

Ser Arg Gly Thr Pro Val Asp Glu Arg Leu Phe Leu Ile Val Arg Val
1               5                   10                  15

Thr Val Gln Leu Ser His Pro
            20

<210> SEQ ID NO 72
<211> LENGTH: 22
<212> TYPE: PRT
<213> ORGANISM: Homo sapiens

<400> SEQUENCE: 72

Arg Gly Thr Pro Val Asp Glu Arg Leu Phe Leu Ile Val Arg Val Thr
1               5                   10                  15

Val Gln Leu Ser His Pro
            20

<210> SEQ ID NO 73
<211> LENGTH: 21
<212> TYPE: PRT
<213> ORGANISM: Homo sapiens
```

```
<400> SEQUENCE: 73

Gly Thr Pro Val Asp Glu Arg Leu Phe Leu Ile Val Arg Val Thr Val
1               5                   10                  15

Gln Leu Ser His Pro
            20

<210> SEQ ID NO 74
<211> LENGTH: 20
<212> TYPE: PRT
<213> ORGANISM: Homo sapiens

<400> SEQUENCE: 74

Arg Gly Thr Pro Val Asp Glu Arg Leu Phe Leu Ile Val Arg Val Thr
1               5                   10                  15

Val Gln Leu Ser
            20

<210> SEQ ID NO 75
<211> LENGTH: 18
<212> TYPE: PRT
<213> ORGANISM: Homo sapiens

<400> SEQUENCE: 75

Arg Gly Thr Pro Val Asp Glu Arg Leu Phe Leu Ile Val Arg Val Thr
1               5                   10                  15

Val Gln

<210> SEQ ID NO 76
<211> LENGTH: 17
<212> TYPE: PRT
<213> ORGANISM: Homo sapiens

<400> SEQUENCE: 76

Ser Arg Gly Thr Pro Val Asp Glu Arg Leu Phe Leu Ile Val Arg Val
1               5                   10                  15

Thr

<210> SEQ ID NO 77
<211> LENGTH: 18
<212> TYPE: PRT
<213> ORGANISM: Homo sapiens

<400> SEQUENCE: 77

Val Arg Val Thr Val Gln Leu Ser His Pro Ala Asp Met Gln Leu Val
1               5                   10                  15

Leu Arg

<210> SEQ ID NO 78
<211> LENGTH: 18
<212> TYPE: PRT
<213> ORGANISM: Homo sapiens

<400> SEQUENCE: 78

Pro Gln Leu Ser Arg Gly Thr Pro Val Asp Glu Arg Leu Phe Leu Ile
1               5                   10                  15

Val Arg

<210> SEQ ID NO 79
<211> LENGTH: 30
<212> TYPE: PRT
```

<213> ORGANISM: Homo sapiens

<400> SEQUENCE: 79

Thr Pro Val Asp Glu Arg Leu Phe Leu Ile Val Arg Val Thr Val Gln
1               5                   10                  15

Leu Ser His Pro Ala Asp Met Gln Leu Val Leu Arg Lys Arg
            20                  25                  30

<210> SEQ ID NO 80
<211> LENGTH: 16
<212> TYPE: PRT
<213> ORGANISM: Pan troglodytes

<400> SEQUENCE: 80

Thr Pro Ala Asp Glu Arg Leu Phe Leu Ile Val Arg Val Thr Val Gln
1               5                   10                  15

<210> SEQ ID NO 81
<211> LENGTH: 16
<212> TYPE: PRT
<213> ORGANISM: Macaca mulatta

<400> SEQUENCE: 81

Thr Pro Ala Asp Glu Arg Leu Phe Leu Ile Val Arg Val Thr Val Gln
1               5                   10                  15

<210> SEQ ID NO 82
<211> LENGTH: 16
<212> TYPE: PRT
<213> ORGANISM: Canis lupus

<400> SEQUENCE: 82

Thr Pro Ala Asp Glu Arg Val Tyr Leu Ile Val Arg Val Thr Val Gln
1               5                   10                  15

<210> SEQ ID NO 83
<211> LENGTH: 16
<212> TYPE: PRT
<213> ORGANISM: Bos Taurus

<400> SEQUENCE: 83

Thr Pro Val Asp Glu Arg Val Phe Leu Ile Val Arg Val Thr Val Gln
1               5                   10                  15

<210> SEQ ID NO 84
<211> LENGTH: 16
<212> TYPE: PRT
<213> ORGANISM: Mus musculus

<400> SEQUENCE: 84

Thr Pro Ala Asp Glu Arg Val Phe Leu Ile Leu Arg Val Thr Val Gln
1               5                   10                  15

<210> SEQ ID NO 85
<211> LENGTH: 16
<212> TYPE: PRT
<213> ORGANISM: Rattus norvegicus

<400> SEQUENCE: 85

Thr Pro Ala Asp Glu Arg Val Phe Leu Ile Leu Arg Val Ala Val Gln
1               5                   10                  15

<210> SEQ ID NO 86
<211> LENGTH: 16

```
<212> TYPE: PRT
<213> ORGANISM: Gallus gallus

<400> SEQUENCE: 86

Thr Ala Ala Asp Glu Arg Val Tyr Leu Ile Val Arg Ala Thr Val Gln
1               5                   10                  15

<210> SEQ ID NO 87
<211> LENGTH: 16
<212> TYPE: PRT
<213> ORGANISM: Danio rerio

<400> SEQUENCE: 87

Thr Glu Ala Asn Glu Arg Val Tyr Leu Ile Leu Arg Thr Thr Val Arg
1               5                   10                  15

<210> SEQ ID NO 88
<211> LENGTH: 16
<212> TYPE: PRT
<213> ORGANISM: Gorilla gorilla

<400> SEQUENCE: 88

Thr Pro Ala Asp Glu Arg Leu Phe Leu Ile Val Arg Val Thr Val Gln
1               5                   10                  15

<210> SEQ ID NO 89
<211> LENGTH: 16
<212> TYPE: PRT
<213> ORGANISM: Echinops telfairi

<400> SEQUENCE: 89

Thr Pro Ser Asp Glu Arg Leu Phe Leu Ile Val Arg Val Thr Val Gln
1               5                   10                  15

<210> SEQ ID NO 90
<211> LENGTH: 16
<212> TYPE: PRT
<213> ORGANISM: Hipposideros armiger

<400> SEQUENCE: 90

Thr Pro Ala Asp Glu Arg Leu Phe Leu Ile Val Arg Val Thr Val Gln
1               5                   10                  15

<210> SEQ ID NO 91
<211> LENGTH: 16
<212> TYPE: PRT
<213> ORGANISM: Capra hircus

<400> SEQUENCE: 91

Thr Pro Val Asp Glu Arg Val Phe Leu Ile Val Arg Val Thr Val Gln
1               5                   10                  15

<210> SEQ ID NO 92
<211> LENGTH: 16
<212> TYPE: PRT
<213> ORGANISM: Rhinolophus sinicus

<400> SEQUENCE: 92

Thr Pro Ala Asp Glu Arg Leu Phe Leu Ile Val Arg Val Thr Val Gln
1               5                   10                  15

<210> SEQ ID NO 93
<211> LENGTH: 16
<212> TYPE: PRT
<213> ORGANISM: Pteropus alecto
```

<400> SEQUENCE: 93

Thr Pro Ala Asp Glu Arg Val Phe Leu Ile Val Arg Val Thr Val Gln
1               5                   10                  15

<210> SEQ ID NO 94
<211> LENGTH: 23
<212> TYPE: PRT
<213> ORGANISM: Homo sapiens

<400> SEQUENCE: 94

Ser Arg Gly Thr Pro Val Asp Glu Arg Leu Phe Leu Ile Val Arg Val
1               5                   10                  15

Thr Val Gln Leu Ser His Pro
            20

<210> SEQ ID NO 95
<211> LENGTH: 23
<212> TYPE: PRT
<213> ORGANISM: Pan troglodytes

<400> SEQUENCE: 95

Ser Arg Gly Thr Pro Ala Asp Glu Arg Leu Phe Leu Ile Val Arg Val
1               5                   10                  15

Thr Val Gln Leu Ser His Pro
            20

<210> SEQ ID NO 96
<211> LENGTH: 23
<212> TYPE: PRT
<213> ORGANISM: Macaca mulatta

<400> SEQUENCE: 96

Ser Lys Gly Thr Pro Ala Asp Glu Arg Leu Phe Leu Ile Val Arg Val
1               5                   10                  15

Thr Val Gln Leu Ser His Pro
            20

<210> SEQ ID NO 97
<211> LENGTH: 23
<212> TYPE: PRT
<213> ORGANISM: Canis lupus

<400> SEQUENCE: 97

Ser Lys Gly Thr Pro Ala Asp Glu Arg Val Tyr Leu Ile Val Arg Val
1               5                   10                  15

Thr Val Gln Leu Ser His Pro
            20

<210> SEQ ID NO 98
<211> LENGTH: 23
<212> TYPE: PRT
<213> ORGANISM: Bos Taurus

<400> SEQUENCE: 98

Ser Lys Gly Thr Pro Val Asp Glu Arg Val Phe Leu Ile Val Arg Val
1               5                   10                  15

Thr Val Gln Leu Ser His Pro
            20

<210> SEQ ID NO 99
<211> LENGTH: 23

```
<212> TYPE: PRT
<213> ORGANISM: Mus musculus

<400> SEQUENCE: 99

Ser Lys Gly Thr Pro Ala Asp Glu Arg Val Phe Leu Ile Leu Arg Val
1               5                   10                  15

Thr Val Gln Leu Ser His Pro
            20

<210> SEQ ID NO 100
<211> LENGTH: 23
<212> TYPE: PRT
<213> ORGANISM: Rattus norvegicus

<400> SEQUENCE: 100

Ser Lys Gly Thr Pro Ala Asp Glu Arg Val Phe Leu Ile Leu Arg Val
1               5                   10                  15

Ala Val Gln Leu Ser His Pro
            20

<210> SEQ ID NO 101
<211> LENGTH: 23
<212> TYPE: PRT
<213> ORGANISM: Gallus gallus

<400> SEQUENCE: 101

Ser Lys Gly Thr Ala Ala Asp Glu Arg Val Tyr Leu Ile Val Arg Ala
1               5                   10                  15

Thr Val Gln Leu Ser His Pro
            20

<210> SEQ ID NO 102
<211> LENGTH: 23
<212> TYPE: PRT
<213> ORGANISM: Danio rerio

<400> SEQUENCE: 102

Asn Arg Val Thr Glu Ala Asn Glu Arg Val Tyr Leu Ile Leu Arg Thr
1               5                   10                  15

Thr Val Arg Leu Ser His Pro
            20

<210> SEQ ID NO 103
<211> LENGTH: 23
<212> TYPE: PRT
<213> ORGANISM: Aotus nancymaae

<400> SEQUENCE: 103

Ser Lys Gly Thr Pro Val Asp Glu Arg Leu Phe Leu Ile Val Arg Val
1               5                   10                  15

Thr Val Gln Leu Ser His Pro
            20

<210> SEQ ID NO 104
<211> LENGTH: 23
<212> TYPE: PRT
<213> ORGANISM: Gorilla gorilla

<400> SEQUENCE: 104

Ser Arg Gly Thr Pro Ala Asp Glu Arg Leu Phe Leu Ile Val Arg Val
1               5                   10                  15

Thr Val Gln Leu Ser His Pro
```

<210> SEQ ID NO 105
<211> LENGTH: 23
<212> TYPE: PRT
<213> ORGANISM: Echinops telfairi

<400> SEQUENCE: 105

Ser Arg Gly Thr Pro Ser Asp Glu Arg Leu Phe Leu Ile Val Arg Val
1               5                   10                  15

Thr Val Gln Leu Ser His Pro
            20

<210> SEQ ID NO 106
<211> LENGTH: 23
<212> TYPE: PRT
<213> ORGANISM: Hipposideros armiger

<400> SEQUENCE: 106

Ser Lys Gly Thr Pro Ala Asp Glu Arg Leu Phe Leu Ile Val Arg Val
1               5                   10                  15

Thr Val Gln Leu Ser His Pro
            20

<210> SEQ ID NO 107
<211> LENGTH: 23
<212> TYPE: PRT
<213> ORGANISM: Capra hircus

<400> SEQUENCE: 107

Ser Lys Gly Thr Pro Val Asp Glu Arg Val Phe Leu Ile Val Arg Val
1               5                   10                  15

Thr Val Gln Leu Ser His Pro
            20

<210> SEQ ID NO 108
<211> LENGTH: 23
<212> TYPE: PRT
<213> ORGANISM: Rhinolophus sinicus

<400> SEQUENCE: 108

Ser Lys Gly Thr Pro Ala Asp Glu Arg Leu Phe Leu Ile Val Arg Val
1               5                   10                  15

Thr Val Gln Leu Ser His Pro
            20

<210> SEQ ID NO 109
<211> LENGTH: 23
<212> TYPE: PRT
<213> ORGANISM: Pteropus alecto

<400> SEQUENCE: 109

Ser Arg Gly Thr Pro Ala Asp Glu Arg Val Phe Leu Ile Val Arg Val
1               5                   10                  15

Thr Val Gln Leu Ser His Pro
            20

<210> SEQ ID NO 110
<211> LENGTH: 20
<212> TYPE: PRT
<213> ORGANISM: Artificial sequence
<220> FEATURE:
<223> OTHER INFORMATION: Synthetic peptide

```
<220> FEATURE:
<221> NAME/KEY: MISC_FEATURE
<222> LOCATION: (1)..(1)
<223> OTHER INFORMATION: MYRISTOYLATION
<220> FEATURE:
<221> NAME/KEY: MOD_RES
<222> LOCATION: (20)..(20)
<223> OTHER INFORMATION: AMIDATION

<400> SEQUENCE: 110

Thr Pro Val Asp Glu Arg Leu Phe Leu Ile Val Arg Val Thr Val Gln
1               5                   10                  15

Leu Ser His Pro
            20

<210> SEQ ID NO 111
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: MYRISTOYLATION
<220> FEATURE:
<221> NAME/KEY: MOD_RES
<222> LOCATION: (20)..(20)
<223> OTHER INFORMATION: AMIDATION

<400> SEQUENCE: 111

Thr Pro Ala Asp Glu Arg Val Phe Leu Ile Leu Arg Val Thr Val Gln
1               5                   10                  15

Leu Ser His Pro
            20

<210> SEQ ID NO 112
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: MYRISTOYLATION
<220> FEATURE:
<221> NAME/KEY: MOD_RES
<222> LOCATION: (20)..(20)
<223> OTHER INFORMATION: AMIDATION

<400> SEQUENCE: 112

Thr Pro Ala Asp Glu Arg Val Phe Leu Ile Leu Arg Val Ala Val Gln
1               5                   10                  15

Leu Ser His Pro
            20

<210> SEQ ID NO 113
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (23)..(23)
<223> OTHER INFORMATION: AMIDATION

<400> SEQUENCE: 113
```

Ser Arg Gly Thr Pro Val Asp Glu Arg Leu Phe Leu Ile Val Arg Val
1               5                   10                  15

Thr Val Gln Leu Ser His Pro
            20

<210> SEQ ID NO 114
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (23)..(23)
<223> OTHER INFORMATION: AMIDATION

<400> SEQUENCE: 114

Ser Lys Gly Thr Pro Ala Asp Glu Arg Val Phe Leu Ile Leu Arg Val
1               5                   10                  15

Thr Val Gln Leu Ser His Pro
            20

<210> SEQ ID NO 115
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (23)..(23)
<223> OTHER INFORMATION: AMIDATION

<400> SEQUENCE: 115

Ser Lys Gly Thr Pro Ala Asp Glu Arg Val Phe Leu Ile Leu Arg Val
1               5                   10                  15

Ala Val Gln Leu Ser His Pro
            20

<210> SEQ ID NO 116
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: MYRISTOYLATION
<220> FEATURE:
<221> NAME/KEY: MOD_RES
<222> LOCATION: (16)..(16)
<223> OTHER INFORMATION: AMIDATION

<400> SEQUENCE: 116

Thr Pro Val Asp Glu Arg Leu Phe Leu Ile Val Arg Val Thr Val Gln
1               5                   10                  15

<210> SEQ ID NO 117
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: MYRISTOYLATION
<220> FEATURE:

```
<221> NAME/KEY: MOD_RES
<222> LOCATION: (1)..(1)
<223> OTHER INFORMATION: AMIDATION

<400> SEQUENCE: 117

Thr Pro Ala Asp Glu Arg Val Phe Leu Ile Leu Arg Val Thr Val Gln
1               5                   10                  15

<210> SEQ ID NO 118
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: MYRISTOYLATION
<220> FEATURE:
<221> NAME/KEY: MOD_RES
<222> LOCATION: (16)..(16)
<223> OTHER INFORMATION: AMIDATION

<400> SEQUENCE: 118

Thr Pro Ala Asp Glu Arg Val Phe Leu Ile Leu Arg Val Ala Val Gln
1               5                   10                  15

<210> SEQ ID NO 119
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: PEGYLATION

<400> SEQUENCE: 119

Ser Arg Gly Thr Pro Val Asp Glu Arg Leu Phe Leu Ile Val Arg Val
1               5                   10                  15

Thr Val Gln

<210> SEQ ID NO 120
<211> LENGTH: 19
<212> TYPE: PRT
<213> ORGANISM: Artificial sequenc
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: PEGYLATION

<400> SEQUENCE: 120

Ser Lys Gly Thr Pro Ala Asp Glu Arg Val Phe Leu Ile Leu Arg Val
1               5                   10                  15

Thr Val Gln

<210> SEQ ID NO 121
<211> LENGTH: 19
<212> TYPE: PRT
<213> ORGANISM: Artificial sequenc
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: PEGYLATION
```

<400> SEQUENCE: 121

Ser Lys Gly Thr Pro Ala Asp Glu Arg Val Phe Leu Ile Leu Arg Val
1               5                   10                  15

Ala Val Gln

<210> SEQ ID NO 122
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (32)..(32)
<223> OTHER INFORMATION: AMIDATION

<400> SEQUENCE: 122

Arg Gln Ile Lys Ile Trp Phe Gln Asn Arg Arg Met Lys Trp Lys Lys
1               5                   10                  15

Thr Pro Val Asp Glu Arg Leu Phe Leu Ile Val Arg Val Thr Val Gln
            20                  25                  30

<210> SEQ ID NO 123
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (32)..(32)
<223> OTHER INFORMATION: AMIDATION

<400> SEQUENCE: 123

Arg Gln Ile Lys Ile Trp Phe Gln Asn Arg Arg Met Lys Trp Lys Lys
1               5                   10                  15

Thr Pro Ala Asp Glu Arg Val Phe Leu Ile Leu Arg Val Thr Val Gln
            20                  25                  30

<210> SEQ ID NO 124
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (32)..(32)
<223> OTHER INFORMATION: AMIDATION

<400> SEQUENCE: 124

Arg Gln Ile Lys Ile Trp Phe Gln Asn Arg Arg Met Lys Trp Lys Lys
1               5                   10                  15

Thr Pro Ala Asp Glu Arg Val Phe Leu Ile Leu Arg Val Ala Val Gln
            20                  25                  30

<210> SEQ ID NO 125
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (32)..(32)
<223> OTHER INFORMATION: PEGYLATION

<400> SEQUENCE: 125

Arg Gln Ile Lys Ile Trp Phe Gln Asn Arg Arg Met Lys Trp Lys Lys
1               5                   10                  15

Thr Pro Val Asp Glu Arg Leu Phe Leu Ile Val Arg Val Thr Val Gln
                20                  25                  30

<210> SEQ ID NO 126
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (32)..(32)
<223> OTHER INFORMATION: PEGYLATION

<400> SEQUENCE: 126

Arg Gln Ile Lys Ile Trp Phe Gln Asn Arg Arg Met Lys Trp Lys Lys
1               5                   10                  15

Thr Pro Ala Asp Glu Arg Val Phe Leu Ile Leu Arg Val Thr Val Gln
                20                  25                  30

<210> SEQ ID NO 127
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (32)..(32)
<223> OTHER INFORMATION: PEGYLATION

<400> SEQUENCE: 127

Arg Gln Ile Lys Ile Trp Phe Gln Asn Arg Arg Met Lys Trp Lys Lys
1               5                   10                  15

Thr Pro Ala Asp Glu Arg Val Phe Leu Ile Leu Arg Val Ala Val Gln
                20                  25                  30

<210> SEQ ID NO 128
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Azidolysine-Vitamin B12
<220> FEATURE:
<221> NAME/KEY: MOD_RES
<222> LOCATION: (23)..(23)
<223> OTHER INFORMATION: AMIDATION

<400> SEQUENCE: 128

Ser Lys Gly Thr Pro Val Asp Glu Arg Leu Phe Leu Ile Val Arg Val
1               5                   10                  15

Thr Val Gln Leu Ser His Pro
                20

<210> SEQ ID NO 129
<211> LENGTH: 23
<212> TYPE: PRT
<213> ORGANISM: Artificial sequence
<220> FEATURE:

```
<223> OTHER INFORMATION: Synthetic peptide
<220> FEATURE:
<221> NAME/KEY: MISC_FEATURE
<222> LOCATION: (2)..(2)
<223> OTHER INFORMATION: Azidolysine-Vitamin B12
<220> FEATURE:
<221> NAME/KEY: MOD_RES
<222> LOCATION: (23)..(23)
<223> OTHER INFORMATION: AMIDATION

<400> SEQUENCE: 129

Ser Lys Gly Thr Pro Ala Asp Glu Arg Val Phe Leu Ile Leu Arg Val
1               5                   10                  15

Thr Val Gln Leu Ser His Pro
            20

<210> SEQ ID NO 130
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Azidolysine-Vitamin B12
<220> FEATURE:
<221> NAME/KEY: MOD_RES
<222> LOCATION: (23)..(23)
<223> OTHER INFORMATION: AMIDATION

<400> SEQUENCE: 130

Ser Lys Gly Thr Pro Ala Asp Glu Arg Val Phe Leu Ile Leu Arg Val
1               5                   10                  15

Ala Val Gln Leu Ser His Pro
            20

<210> SEQ ID NO 131
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Ser or Asn
<220> FEATURE:
<221> NAME/KEY: MISC_FEATURE
<222> LOCATION: (2)..(2)
<223> OTHER INFORMATION: Xaa denotes Arg or Lys
<220> FEATURE:
<221> NAME/KEY: MISC_FEATURE
<222> LOCATION: (3)..(3)
<223> OTHER INFORMATION: Xaa denotes Gly or Val
<220> FEATURE:
<221> NAME/KEY: MISC_FEATURE
<222> LOCATION: (5)..(5)
<223> OTHER INFORMATION: Xaa denotes Pro, Ala or Glu
<220> FEATURE:
<221> NAME/KEY: MISC_FEATURE
<222> LOCATION: (6)..(6)
<223> OTHER INFORMATION: Xaa denotes Val, Ala or Ser
<220> FEATURE:
<221> NAME/KEY: MISC_FEATURE
<222> LOCATION: (7)..(7)
<223> OTHER INFORMATION: Xaa denotes Asp or Asn
<220> FEATURE:
<221> NAME/KEY: MISC_FEATURE
<222> LOCATION: (10)..(10)
<223> OTHER INFORMATION: Xaa denotes Leu or Val
<220> FEATURE:
<221> NAME/KEY: MISC_FEATURE
```

<222> LOCATION: (11)..(11)
<223> OTHER INFORMATION: Xaa denotes Phe or Tyr
<220> FEATURE:
<221> NAME/KEY: MISC_FEATURE
<222> LOCATION: (14)..(14)
<223> OTHER INFORMATION: Xaa denotes Val or Leu
<220> FEATURE:
<221> NAME/KEY: MISC_FEATURE
<222> LOCATION: (16)..(16)
<223> OTHER INFORMATION: Xaa denotes Val or Ala
<220> FEATURE:
<221> NAME/KEY: MISC_FEATURE
<222> LOCATION: (17)..(17)
<223> OTHER INFORMATION: Xaa denotes Thr or Ala
<220> FEATURE:
<221> NAME/KEY: MISC_FEATURE
<222> LOCATION: (19)..(19)
<223> OTHER INFORMATION: Xaa denotes Gln or Arg

<400> SEQUENCE: 131

Xaa Xaa Xaa Thr Xaa Xaa Xaa Glu Arg Xaa Xaa Leu Ile Xaa Arg Xaa
1               5                   10                  15

Xaa Val Xaa Leu Ser His Pro
            20

<210> SEQ ID NO 132
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Lys or Arg
<220> FEATURE:
<221> NAME/KEY: MISC_FEATURE
<222> LOCATION: (6)..(6)
<223> OTHER INFORMATION: Xaa denotes Val, Ala or Ser
<220> FEATURE:
<221> NAME/KEY: MISC_FEATURE
<222> LOCATION: (10)..(10)
<223> OTHER INFORMATION: Xaa denotes Leu or Val
<220> FEATURE:
<221> NAME/KEY: MISC_FEATURE
<222> LOCATION: (11)..(11)
<223> OTHER INFORMATION: Xaa denotes Phe or Tyr
<220> FEATURE:
<221> NAME/KEY: MISC_FEATURE
<222> LOCATION: (14)..(14)
<223> OTHER INFORMATION: Xaa denotes Val or Leu
<220> FEATURE:
<221> NAME/KEY: MISC_FEATURE
<222> LOCATION: (17)..(17)
<223> OTHER INFORMATION: Xaa denotes Thr or Ala

<400> SEQUENCE: 132

Ser Xaa Gly Thr Pro Xaa Asp Glu Arg Xaa Xaa Leu Ile Xaa Arg Val
1               5                   10                  15

Xaa Val Gln Leu Ser His Pro
            20

<210> SEQ ID NO 133
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: MYRISTOYLATION
<220> FEATURE:

```
<221> NAME/KEY: MISC_FEATURE
<222> LOCATION: (3)..(3)
<223> OTHER INFORMATION: Xaa denotes Ala or Val
<220> FEATURE:
<221> NAME/KEY: MISC_FEATURE
<222> LOCATION: (7)..(7)
<223> OTHER INFORMATION: Xaa denotes Leu or Val
<220> FEATURE:
<221> NAME/KEY: MISC_FEATURE
<222> LOCATION: (11)..(11)
<223> OTHER INFORMATION: Xaa denotes Val or Leu
<220> FEATURE:
<221> NAME/KEY: MISC_FEATURE
<222> LOCATION: (14)..(14)
<223> OTHER INFORMATION: Xaa denotes Thr or Ala
<220> FEATURE:
<221> NAME/KEY: MOD_RES
<222> LOCATION: (20)..(20)
<223> OTHER INFORMATION: AMIDATION

<400> SEQUENCE: 133

Thr Pro Xaa Asp Glu Arg Xaa Phe Leu Ile Xaa Arg Val Xaa Val Gln
1               5                   10                  15

Leu Ser His Pro
            20

<210> SEQ ID NO 134
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: MYRISTOYLATION
<220> FEATURE:
<221> NAME/KEY: MISC_FEATURE
<222> LOCATION: (3)..(3)
<223> OTHER INFORMATION: Xaa denotes Ala or Val
<220> FEATURE:
<221> NAME/KEY: MISC_FEATURE
<222> LOCATION: (7)..(7)
<223> OTHER INFORMATION: Xaa denotes Leu or Val
<220> FEATURE:
<221> NAME/KEY: MISC_FEATURE
<222> LOCATION: (11)..(11)
<223> OTHER INFORMATION: Xaa denotes Leu or Val
<220> FEATURE:
<221> NAME/KEY: MISC_FEATURE
<222> LOCATION: (14)..(14)
<223> OTHER INFORMATION: Xaa denotes Thr or Ala
<220> FEATURE:
<221> NAME/KEY: MOD_RES
<222> LOCATION: (16)..(16)
<223> OTHER INFORMATION: AMIDATION

<400> SEQUENCE: 134

Thr Pro Xaa Asp Glu Arg Xaa Phe Leu Ile Xaa Arg Val Xaa Val Gln
1               5                   10                  15

<210> SEQ ID NO 135
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Lys or Arg
<220> FEATURE:
<221> NAME/KEY: MISC_FEATURE
<222> LOCATION: (6)..(6)
```

```
<223> OTHER INFORMATION: Xaa denotes Val or Ala
<220> FEATURE:
<221> NAME/KEY: MISC_FEATURE
<222> LOCATION: (10)..(10)
<223> OTHER INFORMATION: Xaa denotes Leu or Val
<220> FEATURE:
<221> NAME/KEY: MISC_FEATURE
<222> LOCATION: (14)..(14)
<223> OTHER INFORMATION: Xaa denotes Leu or Val
<220> FEATURE:
<221> NAME/KEY: MISC_FEATURE
<222> LOCATION: (17)..(17)
<223> OTHER INFORMATION: Xaa denotes Thr or Ala
<220> FEATURE:
<221> NAME/KEY: MISC_FEATURE
<222> LOCATION: (19)..(19)
<223> OTHER INFORMATION: PEGYLATION

<400> SEQUENCE: 135

Ser Xaa Gly Thr Pro Xaa Asp Glu Arg Xaa Phe Leu Ile Xaa Arg Val
1               5                   10                  15

Xaa Val Gln

<210> SEQ ID NO 136
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: Xaa denotes Ala or Val
<220> FEATURE:
<221> NAME/KEY: MISC_FEATURE
<222> LOCATION: (23)..(23)
<223> OTHER INFORMATION: Xaa denotes Leu or Val
<220> FEATURE:
<221> NAME/KEY: MISC_FEATURE
<222> LOCATION: (27)..(27)
<223> OTHER INFORMATION: Xaa denotes Leu or Val
<220> FEATURE:
<221> NAME/KEY: MISC_FEATURE
<222> LOCATION: (30)..(30)
<223> OTHER INFORMATION: Xaa denotes Thr or Ala
<220> FEATURE:
<221> NAME/KEY: MOD_RES
<222> LOCATION: (32)..(32)
<223> OTHER INFORMATION: AMIDATION

<400> SEQUENCE: 136

Arg Gln Ile Lys Ile Trp Phe Gln Asn Arg Arg Met Lys Trp Lys Lys
1               5                   10                  15

Thr Pro Xaa Asp Glu Arg Xaa Phe Leu Ile Xaa Arg Val Xaa Val Gln
            20                  25                  30

<210> SEQ ID NO 137
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: Xaa denotes Ala or Val
<220> FEATURE:
<221> NAME/KEY: MISC_FEATURE
<222> LOCATION: (23)..(23)
<223> OTHER INFORMATION: Xaa denotes Leu or Val
<220> FEATURE:
<221> NAME/KEY: MISC_FEATURE
<222> LOCATION: (27)..(27)
```

```
<223> OTHER INFORMATION: Xaa denotes Leu or Val
<220> FEATURE:
<221> NAME/KEY: MISC_FEATURE
<222> LOCATION: (30)..(30)
<223> OTHER INFORMATION: Xaa denotes Thr or Ala
<220> FEATURE:
<221> NAME/KEY: MISC_FEATURE
<222> LOCATION: (32)..(32)
<223> OTHER INFORMATION: PEGYLATION

<400> SEQUENCE: 137

Arg Gln Ile Lys Ile Trp Phe Gln Asn Arg Arg Met Lys Trp Lys Lys
1               5                   10                  15

Thr Pro Xaa Asp Glu Arg Xaa Phe Leu Ile Xaa Arg Val Xaa Val Gln
            20                  25                  30

<210> SEQ ID NO 138
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Azidolysine-Vitamin B12
<220> FEATURE:
<221> NAME/KEY: MISC_FEATURE
<222> LOCATION: (6)..(6)
<223> OTHER INFORMATION: Xaa denotes Val or Ala
<220> FEATURE:
<221> NAME/KEY: MISC_FEATURE
<222> LOCATION: (10)..(10)
<223> OTHER INFORMATION: Xaa denotes Leu or Val
<220> FEATURE:
<221> NAME/KEY: MISC_FEATURE
<222> LOCATION: (14)..(14)
<223> OTHER INFORMATION: Xaa denotes Leu or Val
<220> FEATURE:
<221> NAME/KEY: MISC_FEATURE
<222> LOCATION: (17)..(17)
<223> OTHER INFORMATION: Xaa denotes Thr or Ala
<220> FEATURE:
<221> NAME/KEY: MOD_RES
<222> LOCATION: (23)..(23)
<223> OTHER INFORMATION: AMIDATION

<400> SEQUENCE: 138

Ser Lys Gly Thr Pro Xaa Asp Glu Arg Xaa Phe Leu Ile Xaa Arg Val
1               5                   10                  15

Xaa Val Gln Leu Ser His Pro
            20
```

What is claimed is:

1. A construct of no more than 65 amino acids comprising the amino acid sequence Thr-Pro-Xaa$_1$-Asp-Glu-Arg-Xaa$_2$-Xaa$_3$-Leu-Ile-Xaa$_4$-Arg-Val-Xaa$_5$-Val-Xaa$_6$ (SEQ ID NO:2) operably linked to
   (a) one or more carrier moieties,
   (b) one or more stabilizing moieties, or
   (c) a combination of (a) and (b),
   wherein Xaa$_1$ is Val, Ala or Ser; Xaa$_2$ is Leu or Val; Xaa$_3$ is Phe or Tyr; Xaa$_4$ is Leu or Val; Xaa$_5$ is Thr or Ala; and Xaa$_6$ is Gln or Arg.

2. The construct of claim 1, wherein the one or more carrier moieties comprise a cell penetrating peptide, a lipid, Vitamin$_{12}$, or a combination thereof.

3. The construct of claim 2, wherein the cell penetrating peptide comprises a peptide of SEQ ID NO:4-60.

4. The construct of claim 1, wherein the one or more stabilizing moieties comprise a peptide, post-translational modification, non-natural amino acid residue, a macromolecule or a combination thereof.

5. The construct of claim 4, wherein the post-translational modification comprises N-terminal acetylation or C-terminal amidation.

6. The construct of claim 4, wherein the non-natural amino acid residue comprises a D-amino acid residue.

7. The construct of claim 4, wherein the macromolecule comprises polyethylene glycol, polysialic acid, hydroxyethyl starch, albumin or an immunoglobulin fragment.

8. The construct of claim 1, wherein said construct comprises the amino acid sequence TPVDERLFLIVRVTVQ (SEQ ID NO:3).

9. The construct of claim 8, wherein said construct is SRGTPVDERLFLIVRVTVQLSHP-NH$_2$ (SEQ ID NO:113).

10. A pharmaceutical composition comprising the construct of claim 1 and a pharmaceutically acceptable excipient.

11. A method for inhibiting angiogenesis comprising contacting cells or tissue with an effective amount of a construct of claim 1 thereby inhibiting angiogenesis in the cells or tissue.

12. A method of treating a disease or condition in a subject characterized by excessive vascularity comprising administering to the subject an effective amount of a construct of claim 1 thereby treating the disease or condition.

13. The method of claim 12, wherein the disease or condition is an inflammatory disease, cancer, or retinal vasculopathy.

* * * * *